United States Patent
Kopkalli et al.

(10) Patent No.: US 11,987,553 B2
(45) Date of Patent: May 21, 2024

(54) METHODS FOR REMOVAL OF SULFUR DIOXIDE ($SO_2$) FROM TRIFLUOROACETYL CHLORIDE (TFAC)

(71) Applicant: Honeywell International Inc., Charlotte, NC (US)

(72) Inventors: Haluk Kopkalli, Staten Island, NY (US); Haiyou Wang, Amherst, NY (US); Terris Yang, East Amherst, NY (US); Jennifer W. McClaine, Branchburg, NJ (US); Richard Wilcox, West Caldwell, NJ (US); Joshua Close, Cheektowaga, NY (US); Rajendar Mallepally, Charlotte, NC (US)

(73) Assignee: Honeywell International Inc., Charlotte, NC (US)

( * ) Notice: Subject to any disclaimer, the term of this patent is extended or adjusted under 35 U.S.C. 154(b) by 38 days.

(21) Appl. No.: 17/466,704

(22) Filed: Sep. 3, 2021

(65) Prior Publication Data
US 2022/0081386 A1     Mar. 17, 2022

Related U.S. Application Data

(60) Provisional application No. 63/222,801, filed on Jul. 16, 2021, provisional application No. 63/077,352, filed on Sep. 11, 2020.

(51) Int. Cl.
*C07C 71/00* (2006.01)
*B01D 3/36* (2006.01)
(Continued)

(52) U.S. Cl.
CPC .............. *C07C 71/00* (2013.01); *B01D 3/36* (2013.01); *B01D 53/02* (2013.01); *B01J 20/18* (2013.01);
(Continued)

(58) Field of Classification Search
None
See application file for complete search history.

(56) References Cited

U.S. PATENT DOCUMENTS 3,160,659 A * 12/1964 Dittman .................. C07C 53/48
562/859
3,725,475 A * 4/1973 Paucksch ................ C07C 51/58
562/859
(Continued)

FOREIGN PATENT DOCUMENTS

DE     1020970   * 12/1957 ............. C07C 51/58
WO    2011/149711 A2   12/2011

OTHER PUBLICATIONS

International Preliminary Report on Patentability received for PCT Patent Application No. PCT/US2021/071421, dated Mar. 23, 2021, 7 pages.
(Continued)

*Primary Examiner* — Amy C Bonaparte
(74) *Attorney, Agent, or Firm* — Faegre Drinker Biddle & Reath LLP

(57) ABSTRACT

Impurities such as sulfur dioxide ($SO_2$) are removed from trifluoroacetyl chloride (TFAC) through distillation, adsorption, or a combination thereof, and/or including the formation of an azeotrope or azeotrope-like composition including effective amounts of sulfur dioxide ($SO_2$) and trifluoroacetyl chloride (TFAC). The trifluoroacetyl chloride (TFAC) thus purified may then be used in the manufacture of trifluoroiodomethane ($CF_3I$). Also disclosed are azeotropes and azeotrope like compositions of sulfur dioxide ($SO_2$) and trifluoroacetyl chloride (TFAC).

20 Claims, 8 Drawing Sheets

(51) Int. Cl.
    *B01D 53/02*     (2006.01)
    *B01J 20/18*     (2006.01)
    *C07C 51/64*     (2006.01)
    *C07C 53/48*     (2006.01)

(52) U.S. Cl.
    CPC .............. *C07C 51/64* (2013.01); *C07C 53/48* (2013.01); *B01D 2253/108* (2013.01)

(56) References Cited

U.S. PATENT DOCUMENTS

| | | | |
|---|---|---|---|
| 3,763,023 A * | 10/1973 | Horsley | C07C 51/46 203/67 |
| 3,829,483 A | 8/1974 | Rammelt et al. | |
| 4,143,067 A * | 3/1979 | Greth | C07C 51/58 562/858 |
| 4,340,548 A * | 7/1982 | Anello | C07C 51/58 562/859 |
| 4,382,897 A * | 5/1983 | Rudolph | C07C 51/58 562/859 |
| 5,785,888 A | 7/1998 | Tsai et al. | |
| 2004/0133058 A1 | 7/2004 | Arlt et al. | |
| 2010/0004155 A1 | 1/2010 | Ishihara et al. | |
| 2020/0062679 A1 | 2/2020 | Nair et al. | |

OTHER PUBLICATIONS

International Search Report and Written Opinion received for PCT Patent Application No. PCT/US2021/071421, dated Dec. 24, 2021, 8 pages.

* cited by examiner

METHODS FOR REMOVAL OF SULFUR DIOXIDE (SO₂) FROM TRIFLUOROACETYL CHLORIDE (TFAC)

CROSS-REFERENCE TO RELATED APPLICATIONS

This application claims priority to U.S. Provisional Application No. 63/222,801, filed Jul. 16, 2021 and U.S. Provisional Application No. 63/077,352, filed Sep. 11, 2020, both of which are herein incorporated by reference in their entireties.

FIELD

The present disclosure pertains to the removal of sulfur dioxide ($SO_2$) as an impurity from trifluoroacetyl chloride (TFAC). The present disclosure further pertains to azeotrope and azeotrope-like compositions of sulfur dioxide ($SO_2$) and trifluoroacetyl chloride (TFAC).

BACKGROUND

Trifluoroiodomethane ($CF_3I$), also known as perfluoromethyliodide, trifluoromethyl iodide, or iodotrifluoromethane, is a useful compound in commercial applications which may be produced industrially from trifluoroacetyl chloride ($CF_3COCl$, TFAC). Trifluoroiodomethane is an environmentally acceptable compound with a low global warming potential and low ozone depletion potential. Trifluoroiodomethane can replace more environmentally damaging materials.

Methods of preparing trifluoroiodomethane are known. In one method, a 2-step process is employed for producing trifluoroiodomethane from trifluoroacetyl chloride.

The process includes a first step of making trifluoroacetyl iodide, as shown below in Equation 1.

$$CF_3COCl + HI \rightarrow CF_3COI + HCl \quad (1)$$

The process includes a second step for making trifluoroiodomethane via the reaction shown in Equation 2.

$$CF_3COI \rightarrow CF_3I + CO \quad (2)$$

In another method, a one-step process is employed for producing trifluoroiodomethane from trifluoroacetyl chloride, as shown below in Equation 3.

$$CF_3COCl + HI \rightarrow CF_3I + CO + HCl \quad (3)$$

Advantageously, the foregoing processes provide higher selectivity for $CF_3I$ than other processes.

However, it has been found that the presence of sulfur dioxide ($SO_2$), an impurity sometimes found in trifluoroacetyl chloride (TFAC), may have a negative effect on the catalysts used in these processes.

SUMMARY

The present disclosure relates to the removal of impurities from trifluoroacetyl chloride (TFAC) and more specifically, pertains to the removal of sulfur dioxide ($SO_2$) from trifluoroacetyl chloride (TFAC) through distillation, adsorption, or a combination thereof, and/or including the formation of an azeotrope or azeotrope-like composition including effective amounts of sulfur dioxide ($SO_2$) and trifluoroacetyl chloride (TFAC), which may be described as a minimum boiling (or maximum pressure) azeotrope. Distillation and adsorption may be used separately or in combination to reduce the amount of sulfur dioxide ($SO_2$) in trifluoroacetyl chloride (TFAC) to desired levels. The trifluoroacetyl chloride (TFAC) thus purified may then be used in the manufacture of trifluoroacetyl iodide ($CF_3COI$) and/or trifluoroiodomethane ($CF_3I$).

The present disclosure also relates to a composition comprising an azeotrope or azeotrope-like composition consisting essentially of effective amounts of trifluoroacetyl chloride (TFAC) and sulfur dioxide ($SO_2$).

The azeotrope or azeotrope-like composition has a boiling point of about 10.0° C.±3° C. at a pressure of about 45 psia±0.3 psia.

The azeotrope or azeotrope-like composition may comprise, consist essentially of, or consist of from about 25 wt. % to about 99 wt. % trifluoroacetyl chloride (TFAC) and from about 1 wt. % to about 75 wt. % sulfur dioxide ($SO_2$), from about 48 wt. % to about 90 wt. % trifluoroacetyl chloride (TFAC) and from about 10 wt. % to about 52 wt. % sulfur dioxide ($SO_2$), or from about 68 wt. % to about 78 wt. % trifluoroacetyl chloride (TFAC) and from about 22 wt. % to about 32 wt. % sulfur dioxide ($SO_2$).

A method of forming an azeotrope or azeotrope-like composition includes the step of combining trifluoroacetyl chloride (TFAC) and sulfur dioxide ($SO_2$) to form an azeotrope or azeotrope-like composition consisting essentially of trifluoroacetyl chloride (TFAC) and sulfur dioxide ($SO_2$) having a boiling point of about 10.0° C.±3° C. at a pressure of about 45 psia±0.3 psia.

The present disclosure further relates to methods of removing sulfur dioxide ($SO_2$) from trifluoroacetyl chloride (TFAC), the method comprising at least one of distillation, adsorption, or a combination thereof. Distillation and adsorption may be performed separately or combined in order to reach the desired level of sulfur dioxide ($SO_2$) in trifluoroacetyl chloride (TFAC). For example, distillation alone may be performed, as may adsorption alone. Distillation may be followed by adsorption. Alternatively, adsorption may be followed by distillation. In a further alternative, multiple distillation and adsorption steps may be combined.

The present disclosure further relates to methods of removing sulfur dioxide ($SO_2$) from trifluoroacetyl chloride (TFAC) either upstream of a reaction of trifluoroacetyl chloride (TFAC) and hydrogen iodide (HI), downstream of the reaction, or a combination thereof. The sulfur dioxide ($SO_2$) may be removed from the trifluoroacetyl chloride (TFAC) by distillation, adsorption, or combinations thereof. For example, distillation alone may be performed, as may adsorption alone. Distillation may be followed by adsorption. Alternatively, adsorption may be followed by distillation. In a further alternative, multiple distillation and adsorption steps may be combined.

DETAILED DESCRIPTION

Figure 1:
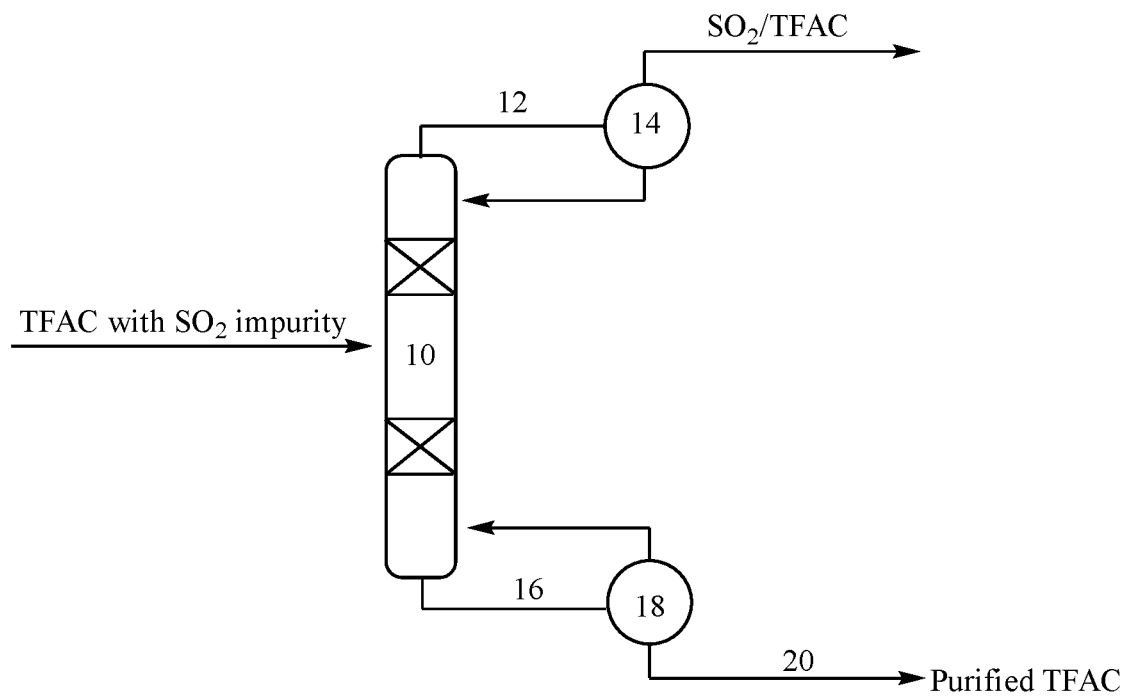
FIG. 1 illustrates an exemplary method for purifying trifluoroacetyl chloride (TFAC) by distillation.

The present disclosure relates to the removal of impurities from trifluoroacetyl chloride (TFAC) and more specifically, pertains to the removal of sulfur dioxide ($SO_2$) from trifluoroacetyl chloride (TFAC) through distillation, adsorption, or a combination thereof, and/or including the formation of an azeotrope or azeotrope-like composition including effective amounts of sulfur dioxide ($SO_2$) and trifluoroacetyl chloride (TFAC).

It has been found that sulfur dioxide ($SO_2$) may interfere with catalytic processes to manufacture trifluoroiodomethane ($CF_3I$) in the two-step and one-step processes set forth above, wherein trifluoroacetyl chloride (TFAC) purified by the methods of the present disclosure may provide an effective starting material for the production of trifluoroiodomethane ($CF_3I$).

1. Removal of Sulfur Dioxide ($SO_2$) Prior to Formation of Trifluoroacetyl Iodide (TFAI)

One method by which trifluoroacetyl chloride (TFAC) may be purified includes the formation of an azeotrope or azeotrope-like composition with sulfur dioxide ($SO_2$). This azeotrope or azeotrope-like composition may be removed from the bulk trifluoroacetyl chloride (TFAC) via distillation. Another method by which sulfur dioxide ($SO_2$) may be removed from trifluoroacetyl chloride (TFAC) includes contacting a mixture of trifluoroacetyl chloride (TFAC) and sulfur dioxide ($SO_2$) with a solid adsorbent or a mixture of two or more solid adsorbents to remove sulfur dioxide ($SO_2$) from the mixture of trifluoroacetyl chloride (TFAC) and sulfur dioxide ($SO_2$). Yet another method by which trifluoroacetyl chloride (TFAC) may be purified includes a combination of these methods. Contacting the mixture of trifluoroacetyl chloride (TFAC) and sulfur dioxide ($SO_2$) with a solid adsorbent may precede or follow distillation. Multiple adsorption steps may be used, with or without distillation.

It has been found that trifluoroacetyl chloride (TFAC) forms homogeneous, minimum boiling azeotrope and azeotrope-like compositions or mixtures with sulfur dioxide ($SO_2$), and the present disclosure provides homogeneous azeotrope or azeotrope-like compositions comprising trifluoroacetyl chloride (TFAC) and sulfur dioxide ($SO_2$). The azeotrope or azeotrope-like compositions may consist essentially of trifluoroacetyl chloride (TFAC) and sulfur dioxide ($SO_2$) or the azeotrope or azeotrope-like compositions may consist of trifluoroacetyl chloride (TFAC) and sulfur dioxide ($SO_2$).

An "azeotrope" composition is a unique combination of two or more components. An azeotrope composition can be characterized in various ways. For example, at a given pressure, an azeotrope composition boils at a constant characteristic temperature which is either greater than the higher boiling point component (maximum boiling azeotrope) or less than the lower boiling point component (minimum boiling azeotrope). At this characteristic temperature the same composition will exist in both the vapor and liquid phases. The azeotrope composition does not fractionate upon boiling or evaporation. Therefore, the components of the azeotrope composition cannot be separated during a phase change.

Alternatively, an azeotrope composition may be characterized as a composition which boils at a characteristic vapor pressure at a given temperature. The vapor pressure may be lower than the lower vapor pressure component (pressure minimum azeotrope) or the vapor pressure may be higher than the higher vapor pressure component (pressure maximum azeotrope). A pressure minimum azeotrope may be referred to as a maximum boiling azeotrope, or vice versa, and a pressure maximum azeotrope may be referred to as a minimum boiling azeotrope, or vice versa.

The behavior of an azeotrope composition is in contrast with that of a non-azeotrope composition in which during boiling or evaporation, the liquid composition changes to a substantial degree.

One of ordinary skill in the art would understand however that at different pressures, both the composition and the boiling point of the azeotrope composition will vary to some extent. Therefore, depending on the temperature and/or pressure, an azeotrope composition can have a variable composition. The skilled person would therefore understand that composition ranges, rather than fixed compositions, can be used to define azeotrope compositions. In addition, an azeotrope may be defined in terms of exact weight percentages of each component of the compositions characterized by a fixed boiling point at a specified pressure.

An "azeotrope-like" composition is a composition of two or more components which behaves substantially as an azeotrope composition. Thus, for the purposes of this disclosure, an azeotrope-like composition is a combination of two or more different components which, when in liquid form under given pressure, will boil at a substantially constant temperature, and which will provide a vapor composition substantially identical to the liquid composition undergoing boiling.

Azeotrope or azeotrope-like compositions can be identified using a number of different methods.

Static Vapor-Liquid Equilibrium Methods are a class of experimental techniques that can be used to identify the presence of azeotrope and azeotrope-like compositions. One such technique, known as the PTx method, collects measurements of the total saturation pressure ("P") exerted by mixtures of known compositions ("x") at fixed temperatures ("T") and cell volumes. (Walas, Phase Equilibria in Chemical Engineering, Butterworth-Heinemann, 1985, pp. 537). Using data collected from the PTx experiment, as well as pure component properties of constituents of the mixtures, the thermodynamic properties of the mixture can be accurately characterized by fitting the component's interaction parameters in a well-defined thermodynamic equation; one such equation is a Helmholtz Energy Equation of State (HEOS) described by E. W. Lemmon et al. (Generalized Model for the Thermodynamic Properties of Mixtures, International Journal of Thermophysics, Vol. 20, 1999, pp. 825-835).

The presence of an azeotrope and its corresponding composition can be observed by plotting saturation pressure measurements from PTx data and saturation pressures described by the HEOS as a function of composition. For a given temperature (isotherm), the presence of an azeotrope composition is identified by the observation of a maximum or minimum in total pressure that is greater or less than the pure saturation pressures of any of the components alone.

As the skilled person will appreciate, the identification of the azeotrope or azeotrope-like composition is made by the comparison of the change in the boiling point of the composition on addition of the second component to the first component, relative to the boiling point of the first component. Thus, it is not necessary that the system be calibrated to the reported boiling point of the particular components in order to measure the change in boiling point.

The present disclosure provides an azeotrope or azeotrope-like composition which comprises effective amounts of trifluoroacetyl chloride (TFAC) and sulfur dioxide ($SO_2$) to form an azeotrope or azeotrope-like composition. As used herein, the term "effective amount" is an amount of each component which, when combined with the other component, results in the formation of an azeotrope or azeotrope-like mixture.

The present azeotrope or azeotrope-like compositions may consist essentially of combinations of trifluoroacetyl chloride (TFAC) and sulfur dioxide ($SO_2$) or consist of combinations of trifluoroacetyl chloride (TFAC) and sulfur dioxide ($SO_2$).

As used herein, the term "consisting essentially of", with respect to the components of an azeotrope or azeotrope-like composition or mixture, means the composition contains the indicated components in an azeotrope or azeotrope-like ratio, and may contain additional components provided that the additional components do not form new azeotrope or azeotrope-like systems. For example, azeotrope mixtures consisting essentially of two compounds are those that form binary azeotropes, which optionally may include one or more additional components, provided that the additional components do not render the mixture non-azeotropic and do not form an azeotrope with either or both of the compounds (e.g., do not form a ternary or higher azeotrope).

The azeotrope or azeotrope-like composition having a boiling point of about 10.0° C.±3° C. at a pressure of about 45 psia±0.3 psia may comprise, consist essentially of, or consist of, from about 25 wt. % to about 99 wt. % trifluoroacetyl chloride (TFAC) and from about 1 wt. % to about 75 wt. % sulfur dioxide ($SO_2$), from about 48 wt. % to about 90 wt. % trifluoroacetyl chloride (TFAC) and from about 10 wt. % to about 52 wt. % sulfur dioxide ($SO_2$), or from about 68 wt. % to about 78 wt. % trifluoroacetyl chloride (TFAC) and from about 22 wt. % to about 32 wt. % sulfur dioxide ($SO_2$).

Alternatively, the azeotrope or azeotrope-like composition having a boiling point of about 10.0° C.±3° C. at a pressure of about 45 psia±0.3 psia may comprise, consist essentially of, or consist of, from about 24.5 wt. % to about 94.9 wt. % trifluoroacetyl chloride (TFAC) and from about 5.1 wt. % to about 75.5 wt. % sulfur dioxide ($SO_2$), or from about 47.9 wt. % to about 89.7 wt. % trifluoroacetyl chloride (TFAC) and from about 10.3 wt. % to about 52.1 wt. % sulfur dioxide ($SO_2$).

The present disclosure also provides a composition comprising the azeotrope or azeotrope-like composition. For example, there is provided a composition comprising at low as 1 ppm of the azeotrope or azeotrope-like compositions, 10 ppm of the azeotrope or azeotrope-like compositions, 25 ppm of the azeotrope or azeotrope-like compositions, or as high as 50 ppm of the azeotrope or azeotrope-like compositions, 100 ppm of the azeotrope or azeotrope-like compositions, 1000 ppm of the azeotrope or azeotrope-like compositions, 1 wt. % of the azeotrope or azeotrope-like compositions, 5 wt. % or more of the azeotrope or azeotrope-like compositions.

Following the separation of the azeotrope or azeotrope-like composition from another composition, the azeotropic composition may include at least 10 wt. % of the azeotrope or azeotrope-like compositions, or at least about 20 wt. % of the azeotrope or azeotrope-like compositions, or at least about 50 wt. % of the azeotrope or azeotrope-like compositions, or at least about 70 wt. % of the azeotrope or azeotrope-like compositions, or at least about 90 wt. % of the azeotrope or azeotrope-like compositions.

The azeotrope or azeotrope-like composition comprising, consisting essentially of, or consisting of effective amounts of trifluoroacetyl chloride (TFAC) and sulfur dioxide ($SO_2$) disclosed herein may be used for separating impurities, including sulfur dioxide ($SO_2$), from trifluoroacetyl chloride (TFAC).

In particular, an azeotrope or azeotrope-like composition comprising, consisting essentially of, or consisting of effective amounts of trifluoroacetyl chloride (TFAC) and sulfur dioxide ($SO_2$) may be formed from a composition including one or both of trifluoroacetyl chloride (TFAC) and sulfur dioxide ($SO_2$), optionally together with one or more other chemical compounds other than trifluoroacetyl chloride (TFAC) and sulfur dioxide ($SO_2$), such as other impurities. Following the formation of the azeotrope or azeotrope-like composition, the azeotrope or azeotrope-like composition may be separated from the other chemical compounds by a suitable method, such as by distillation or fractionation.

The present disclosure provides a method of separating sulfur dioxide ($SO_2$) as an impurity from a crude composition of trifluoroacetyl chloride (TFAC) which includes sulfur dioxide ($SO_2$) as an impurity, together with any additional impurities, if present. The sulfur dioxide ($SO_2$) may be present in the crude composition of trifluoroacetyl chloride (TFAC) in an amount of about 5 ppm or greater, about 50 ppm or greater, about 100 ppm or greater, about 500 ppm or greater, about 1000 ppm or greater, about 2000 ppm or greater, about 3000 ppm or greater, or about 5000 ppm or greater.

One method comprises the steps of providing crude trifluoroacetyl chloride (TFAC), sulfur dioxide ($SO_2$) as an impurity, and any other impurities, if present; conveying the crude trifluoroacetyl chloride (TFAC) to a distillation column; collecting the distillate from the distillation column, the distillate comprising sulfur dioxide ($SO_2$), or an azeotrope or azeotrope-like mixture of sulfur dioxide ($SO_2$) and trifluoroacetyl chloride (TFAC); and collecting the bottoms product from the distillation column, the bottoms product consisting essentially of trifluoroacetyl chloride (TFAC).

Another method comprises the steps of providing a crude composition comprising trifluoroacetyl chloride (TFAC), sulfur dioxide ($SO_2$) as an impurity, and any other impurities, if present, and subjecting the crude composition to conditions effective to form an azeotrope or azeotrope-like composition consisting essentially of, or consisting of, effective amounts of trifluoroacetyl chloride (TFAC) and sulfur dioxide ($SO_2$), and separating the azeotrope or azeotrope-like composition from the crude composition by a separation technique such as distillation, or fractionation, for example. Thereafter, the azeotrope or azeotrope-like composition may be subjected to further separation or purification steps to obtain purified trifluoroacetyl chloride (TFAC).

A further method of separating trifluoroacetyl chloride (TFAC) and sulfur dioxide ($SO_2$) from a feed stream including trifluoroacetyl chloride (TFAC) and sulfur dioxide ($SO_2$) is illustrated in FIG. 1. This method may include the formation of an azeotrope or azeotrope-like composition or may not include the formation of an azeotrope or azeotrope-like composition. The method includes an initial step of conveying a feed stream including trifluoroacetyl chloride (TFAC) and sulfur dioxide ($SO_2$) to a distillation column 10. A bottoms product 16 may be passed through a reboiler 18 and a portion of it recycled back to the column 10 and another portion of it collected as a bottoms product stream 20. The bottoms product stream 20 consists essentially of trifluoroacetyl chloride (TFAC). The overhead stream 12 is passed through a condenser 14 and a portion of it refluxed back to the column 10 and the remainder collected as an overhead product stream. The overhead product stream comprises an azeotrope or azeotrope-like composition consisting essentially of effective amounts of trifluoroacetyl chloride (TFAC) and sulfur dioxide ($SO_2$). The product stream may further comprise excess trifluoroacetyl chloride (TFAC). The column may be operated under various temperature and pressure conditions to achieve the desired separation.

The bottoms product stream 20 may include sulfur dioxide ($SO_2$) in an amount of about 100 ppm or less, about 50 ppm or less, about 10 ppm or less, or about 1 ppm or less.

In another example, the present disclosure provides a method of separating sulfur dioxide ($SO_2$) as an impurity from a crude composition of trifluoroacetyl chloride (TFAC) which includes sulfur dioxide ($SO_2$) as an impurity, together with at least one additional impurity, comprising the steps of providing a composition of crude trifluoroacetyl chloride (TFAC), sulfur dioxide ($SO_2$) as an impurity, and at least one additional impurity, and contacting the crude composition with a solid adsorbent.

Suitable adsorbents may include molecular sieves, such as 3 Å molecular sieves available from Acros Organics (also available from Honeywell UOP); 4 Å and XH-9 molecular sieves available from Honeywell UOP, 10 Å molecular sieves available from Grace Davison, and carbon molecular sieves, such as JEChem MSC-3K 172 carbon molecular sieves available from Osaka Gas Chemicals; activated alumina, such as SAS40 1/8" Alumina available from BASF; zeolite ammonium powders, such as CBV5524G CY available from Zeolyst International; and activated charcoal, such as NORIT ROX 0.8 Activated Carbon available from Cabot.

Figure 2:
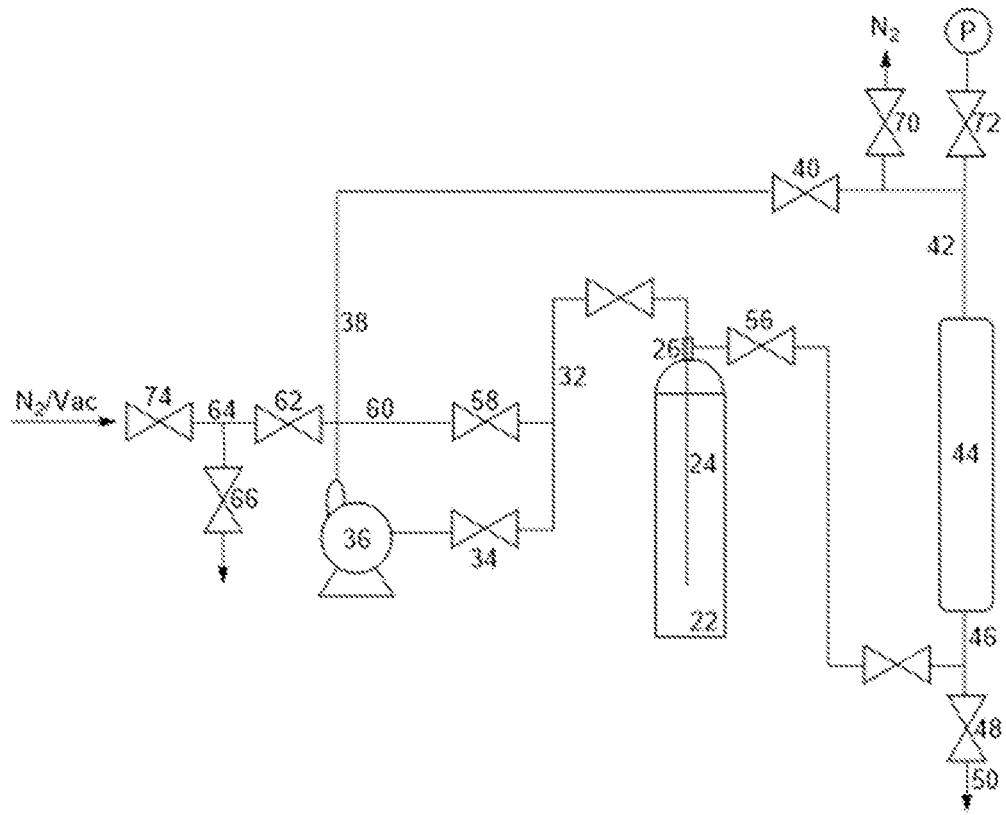
FIG. 2 illustrates an exemplary method for purifying trifluoroacetyl chloride (TFAC) by adsorption of impurities.

In this method, sulfur dioxide ($SO_2$) may be removed from trifluoroacetyl chloride (TFAC) through an adsorption process as shown in FIG. 2. A vessel, such as a cylinder or storage tank 22, is charged with the $SO_2$-containing trifluoroacetyl chloride (TFAC). The liquid draw-off port 26 of the trifluoroacetyl chloride (TFAC) vessel 22 is equipped with a dip-tube 24. The stream of $SO_2$-containing trifluoroacetyl chloride (TFAC) passes through the dip-tube 24, is conveyed through a line 32 and is conveyed to the inlet 34 of a trifluoroacetyl chloride (TFAC) recirculation pump 36. The outlet line 38 of the trifluoroacetyl chloride (TFAC) recirculation pump 36 is connected to valve 40 which may convey the stream 42 of $SO_2$-containing trifluoroacetyl chloride (TFAC) to the adsorption column 44. The outlet 46 of the adsorption column 44 is connected to the vapor port 56 of the vessel 22. A nitrogen gas purge port 70 and pressure gauge 72 are connected to the recirculation pump outlet line 38. A portion of stream 32 may be diverted through valve 58 to line 60 ultimately to pass through the sampling port 66. A vacuum/nitrogen port 74 is also connected to line 60 via valve 62 and line 64.

After the system is pressure checked, $SO_2$-containing trifluoroacetyl chloride (TFAC) is pumped out of the vessel 22 via dip tube 24 and liquid port 26 by the recirculation pump 36, passed through the adsorption column 44, and returned to the trifluoroacetyl chloride (TFAC) vessel 22 via the vapor port 56. Periodically, samples can be taken from the sampling port 66 to analyze the $SO_2$ concentration by thermal conductivity detector-gas chromatography (TCD-GC). After a period of time, when $SO_2$ concentration reaches certain level or the adsorbent is saturated by $SO_2$, the recirculation pump 36 is stopped and the trifluoroacetyl chloride (TFAC) cylinder valves are closed to contain trifluoroacetyl chloride (TFAC) in the vessel 22. The residual trifluoroacetyl chloride (TFAC) in the system is drained to another container (not shown) or vented off to a KOFI scrubber (not shown) connected to drain port 50 through valve 48 and the system is purged with nitrogen gas through port 74. The adsorption column 44 is disconnected from the system and the spent adsorbent is discharged from the column for regeneration. Preferably, a second adsorption column (not shown) in parallel with adsorption column 44 may be used to achieve a continuous adsorption operation.

On a larger scale, the $SO_2$-containing TFAC feed stream may be contacted by the adsorbent. This contact may be mediated via a pump to move the feed stream through a packed bed by pressure differential. Once contacted by the adsorbent, the feed stream may be recirculated from the bed back to the holding vessel until the desired purity is achieved.

The recirculation process (or adsorption process) can be operated at a temperature of about −30° C. or greater, about −20° C. or greater, about −10° C. or greater, about 0° C. or greater, about 10° C. or greater, about 20° C. or less, about 30° C. or less, about 40° C. or less, about 50° C. or less, about 60° C. or less, about 70° C. or less, about 80° C. or less, or about 90° C. or less, preferably from 0° C. to 60° C., and even more preferably, from 20° C. to 40° C.

The recirculation process (or adsorption process) can be operated at a pressure of about 0 psig or greater, about 50 psig or greater, about 100 psig or greater, about 150 psig or greater, about 200 psig or greater, about 250 psig or greater, about 300 psig or less, about 350 psig or less, about 400 psig or less, about 450 psig or less, or about 500 psig or less, preferably from 10 pisg to 200 psig, and even more preferably, from 40 pisg to 100 psig.

The space velocity of $SO_2$-containing trifluoroacetyl chloride (TFAC) flowing through the adsorption column is not critical and may be varied over a wide range. A longer recirculation time may be needed for higher space velocity conditions. Optimal recirculation time may be determined experimentally until the desired $SO_2$ level in the trifluoroacetyl chloride (TFAC) is achieved.

Upon reaching saturation, a solid adsorbent will no longer function. The spent solid adsorbent may optionally be regenerated for re-use. Regeneration may be accomplished by heating the spent solid adsorbent to an elevated temperature under vacuum or in the presence of a purging gas, such as nitrogen, to desorb the adsorbed species, which may include sulfur dioxide ($SO_2$). The desorption temperature may range from 100° C. to 600° C., preferably from 150° C. to 500° C., and more preferably from 300° C. to 400° C.

The purified trifluoroacetyl chloride (TFAC) obtained after adsorption from this method may include sulfur dioxide ($SO_2$) in an amount of about 0.1 wt. % or less, about 0.05 wt. % or less, about 0.03 wt. % or less, about 0.02 wt. % or less, about 0.001 wt. % or less, or about 0 wt. %.

The percentage of sulfur dioxide ($SO_2$) removed from the trifluoroacetyl chloride (TFAC) by adsorption may be about 5% or greater, about 10% or greater, about 20% or greater, about 50% or greater, about 60% or greater, about 70% or greater, about 80% or greater, about 90% or greater, or about 100%.

Figure 3:
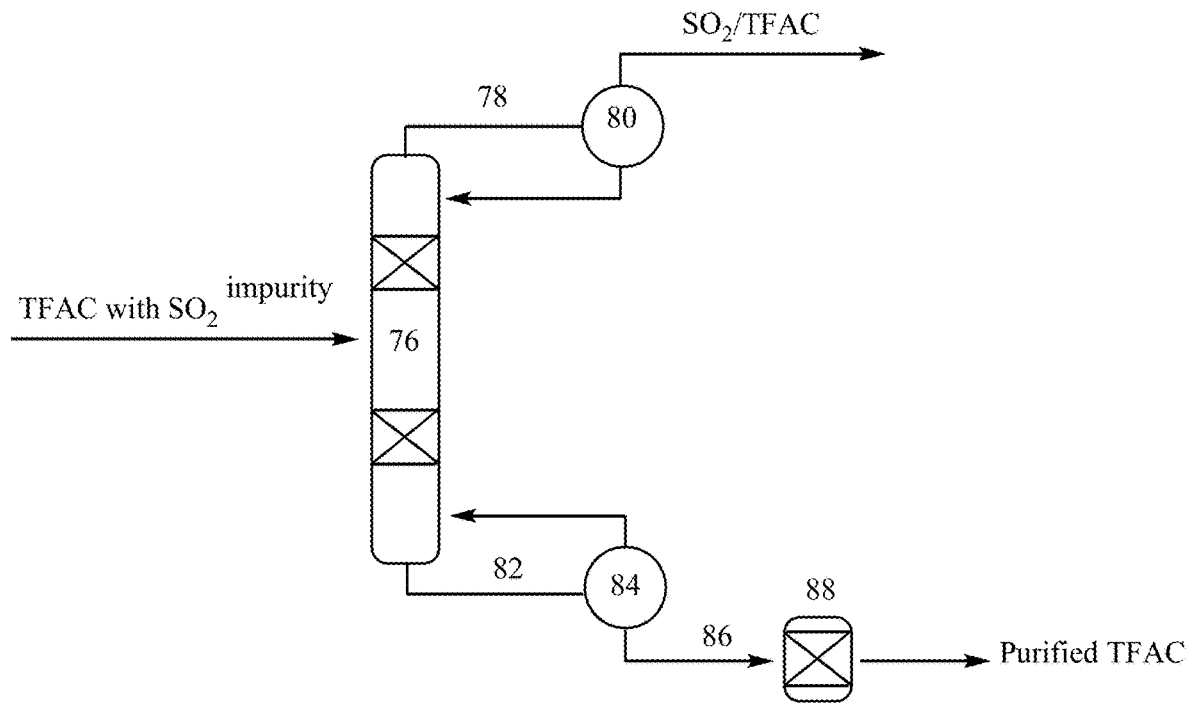
FIG. 3 illustrates an exemplary method for purifying trifluoroacetyl chloride (TFAC) by a combination of distillation and adsorption.

As a further alternative, the methods illustrated in FIGS. 1 and 2 may be combined. For example, as shown in FIG. 3, a feed stream comprising trifluoroacetyl chloride (TFAC) and sulfur dioxide ($SO_2$) may be conveyed to a distillation column 76. A bottoms product 82 may be passed through a reboiler 84 and a portion recycled back to the distillation column 76 and another portion collected as a bottoms product stream 86. The bottoms product stream 86 may be conveyed to an adsorption column 88 to create a product stream consisting essentially of purified trifluoroacetyl chloride (TFAC). The overhead stream 78, comprising the azeotrope or azeotrope-like composition consisting essentially of effective amounts of trifluoroacetyl chloride (TFAC) and sulfur dioxide ($SO_2$), and optionally including excess amounts of trifluoroacetyl chloride (TFAC), may pass through a condenser 80 and a portion refluxed back to the distillation column 76 and another portion purged as the lights stream. The adsorption column 88 may be operated using either a once-through method or a recirculation method.

Figure 4:
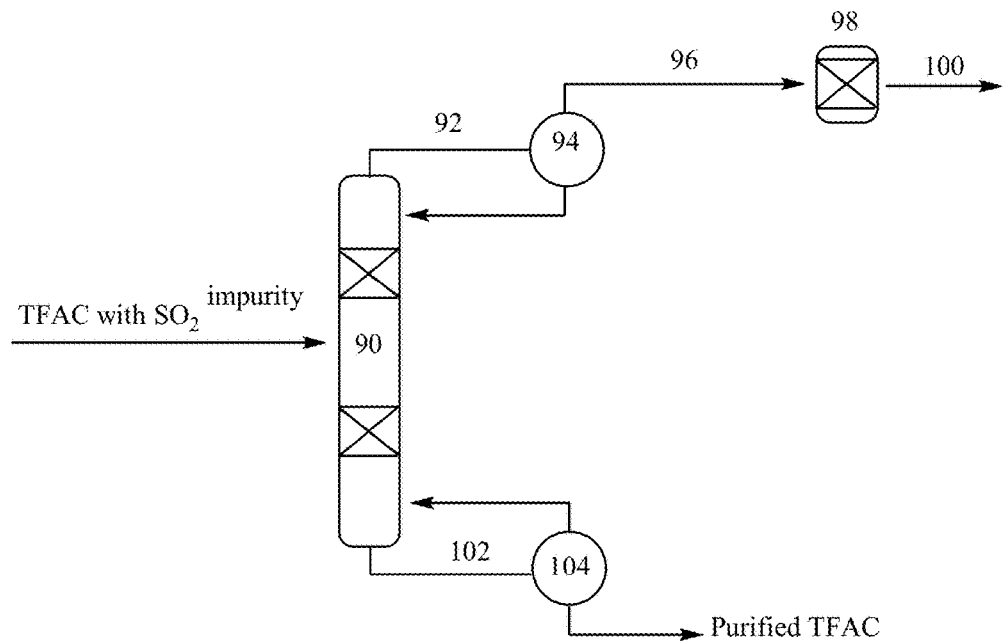
FIG. 4 illustrates a further exemplary method for purifying trifluoroacetyl chloride (TFAC) by a combination of distillation and adsorption.

A different alternative for the combined methods of FIGS. 1 and 2 is shown in FIG. 4. A feed stream comprising trifluoroacetyl chloride (TFAC) and sulfur dioxide ($SO_2$) may be conveyed to a distillation column 90. The bottoms product 102 may be passed through a reboiler 104 and a portion recycled back to the distillation column 90 and another portion collected as a bottoms product stream comprising purified trifluoroacetyl chloride (TFAC). The overhead stream 92 is passed through a condenser 94 and a portion refluxed back to the distillation column 90 and another portion collected as the overhead product stream 96, which comprises an azeotrope or azeotrope-like composition consisting essentially of effective amounts of trifluoroacetyl chloride (TFAC) and sulfur dioxide ($SO_2$) and optionally including excess trifluoroacetyl chloride (TFAC), may be conveyed to an adsorption column 98 to create a product stream 100 consisting essentially of purified trifluoroacetyl chloride (TFAC). The adsorption column 98 may be operated using either a once-through method or a recirculation method.

Figure 5:
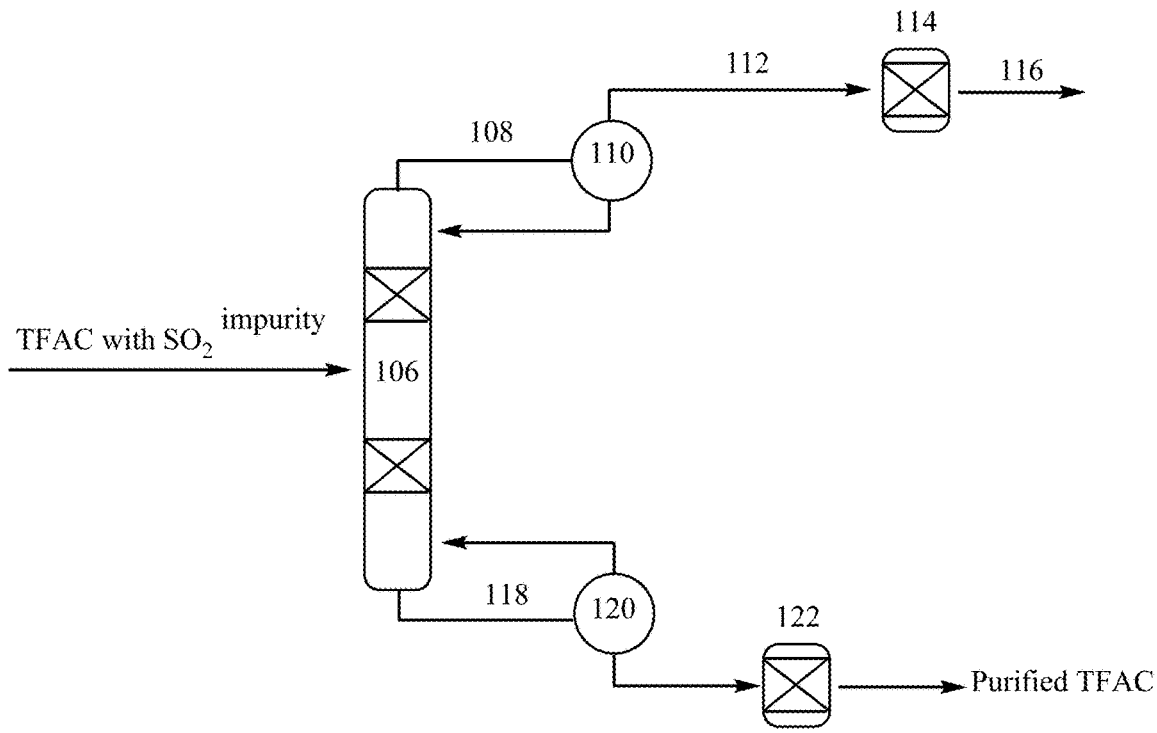
FIG. 5 illustrates a still further exemplary method for purifying trifluoroacetyl chloride (TFAC) by a combination of distillation and adsorption.

A still further alternative for the combined methods is shown in FIG. 5. A feed stream comprising trifluoroacetyl chloride (TFAC) and sulfur dioxide ($SO_2$) may be conveyed to a distillation column 106. The bottoms product 118 may be passed through a reboiler 120 and a portion recycled back to the distillation column 106 and another portion conveyed to an adsorption column 122 to create a product stream consisting essentially of purified trifluoroacetyl chloride (TFAC). The overhead stream 108 is passed through a condenser 110 and a portion refluxed back to the distillation column 106 and another portion is collected as the product stream 112, which is an azeotrope or azeotrope-like composition consisting essentially of effective amounts of trifluoroacetyl chloride (TFAC) and sulfur dioxide ($SO_2$) and optionally including excess trifluoroacetyl chloride (TFAC), may be conveyed to an adsorption column 114 to create a product stream 116 consisting essentially of purified trifluoroacetyl chloride (TFAC). The adsorption columns 122 and 114 may be operated using either a once-through method or a recirculation method.

Figure 6:
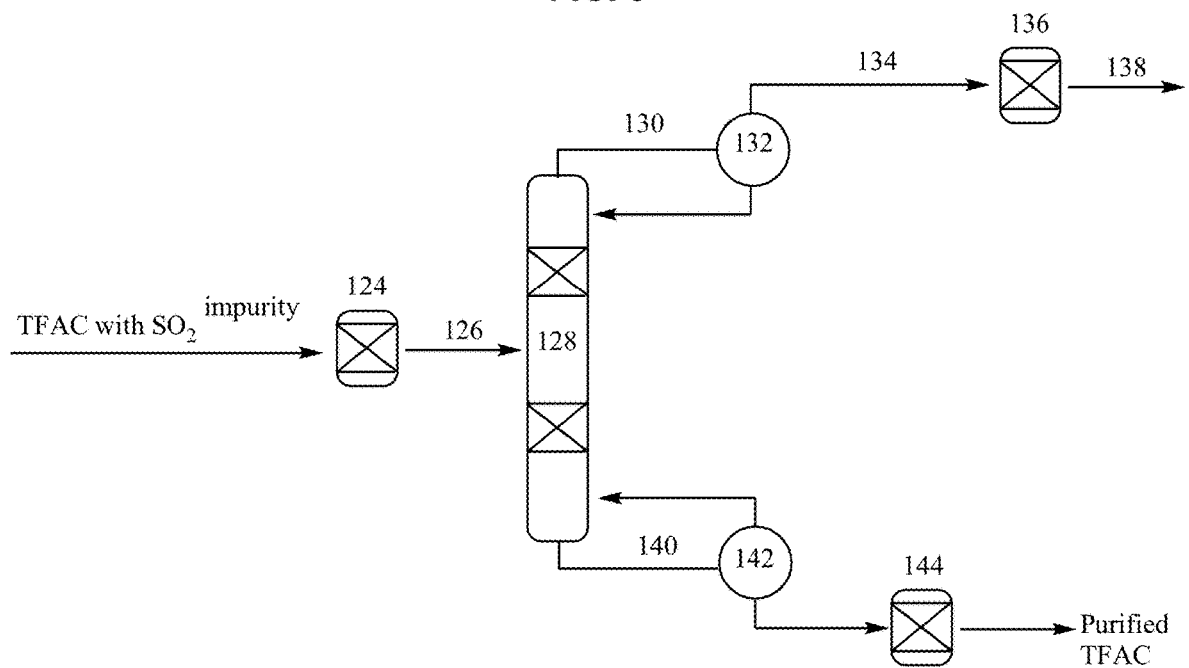
FIG. 6 illustrates a still further exemplary method for purifying trifluoroacetyl chloride (TFAC) by a combination of distillation and adsorption.

Yet another alternative for the combined methods is shown in FIG. 6. A feed stream comprising trifluoroacetyl chloride (TFAC) and sulfur dioxide ($SO_2$) may be conveyed to an adsorption column 124 to produce a purified feed stream 126. The purified feed stream 126 may be conveyed to a distillation column 128. The bottoms product 140 may be passed through a reboiler 142 and a portion recycled back to the distillation column 128 and another portion conveyed to an adsorption column 144 to create a product stream consisting essentially of purified trifluoroacetyl chloride (TFAC). The overhead stream 130 is passed through a condenser 132 and a portion refluxed back to the distillation column 128 and another portion is collected as the product stream 134, which is an azeotrope or azeotrope-like composition consisting essentially of effective amounts of trifluoroacetyl chloride (TFAC) and sulfur dioxide ($SO_2$) and optionally including excess trifluoroacetyl chloride (TFAC), may be conveyed to an adsorption column 136 to create a product stream 138 consisting essentially of purified trifluoroacetyl chloride (TFAC). The adsorption columns 144 and 136 may be operated using either a once-through method or a recirculation method. The position of the first adsorption column shown in FIG. 6 may be replicated in any of the other foregoing methods.

2. Synthesis of Trifluoroacetyl Iodide (TFAI)

As shown in Equation 1, trifluoroacetyl chloride (TFAC) may be reacted with hydrogen iodide (HI) to synthesize trifluoroacetyl iodide (TFAI).

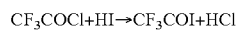

$$CF_3COCl + HI \rightarrow CF_3COI + HCl$$

The process may be a gas-phase process comprising providing a reactant stream comprising hydrogen iodide and at least one trifluoroacetyl halide selected from trifluoroacetyl chloride (TFAC), trifluoroacetyl fluoride (TFAF), trifluoroacetyl bromide (TFAB), and combinations thereof, to produce an intermediate product stream comprising the trifluoroacetyl iodide. (TFAI).

The process may be conducted in a reactor, such as a heated tube reactor comprising a tube made of a metal such as stainless steel, nickel, and/or a nickel alloy, such as a nickel-chromium alloy, a nickel-molybdenum alloy, a nickel-chromium-molybdenum alloy, or a nickel-copper alloy. The tube within the reactor may be heated or the feed materials may be preheated before entering the reactor. The reactor may be any type of packed bed reactor.

The hydrogen iodide and the trifluoroacetyl iodide in the reactant stream may react in the presence of a catalyst contained within the reactor. The catalyst may comprise activated carbon, meso carbon, stainless steel, nickel, nickel-chromium alloy, nickel-chromium-molybdenum alloy, nickel-copper alloy, copper, alumina, platinum, palladium, or carbides, such as metal carbides, such as iron carbide, molybdenum carbide and nickel carbide, and non-metal carbides, such as silicon carbide, or combinations thereof. The catalyst may be in the form of a mesh, pellet, or sphere, contained within the reactor.

The reaction temperature may be as low as about 0° C. or higher, about 25° C. or higher, about 35° C. or higher, about 40° C. or higher, about 50° C. or higher, or about 60° C. or lower, about 90° C. or lower, about 120° C. or lower, about 150° C. or lower, or about 200° C. or lower, or about 250° C. or lower, or any value encompassed by these endpoints.

In an example of this process, fresh hydrogen iodide (HI) and trifluoroacetyl chloride (TFAC) are combined with a recycled mixture comprising HI and TFAC recovered from a distillation train. The combined TFAC/HI mole ratio is provided with an excess of TFAC to give high conversion of the more expensive HI, although equimolar amounts or an excess of HI may be used.

The TFAC/HI ratio may about 1:10 or less, about 1:5 or less, about 1:2 or less, about 1:1 or greater, about 2:1 or greater, about 3:1 or greater, about 4:1 or greater, about 5:1 or greater, about 6:1 or greater, about 7:1 or greater, about 8:1 or greater, about 9:1 or greater, about 10:1 or greater, or any value encompassed by these endpoints. Preferably, the TFAC/HI ratio is from 1:2 to 2:1. More preferably, the TFAC/HI ratio is from 1:1 to 2:1.

The pressure may be about 0 psig or higher, about 1 psig or higher, about 5 psig or higher, about 25 psig or higher, about 50 psig or higher, about 100 psig or higher, about 150 psig or higher, about 200 psig or lower, about 250 psig or lower, about 300 psig or lower, about 350 psig or lower, about 400 psig or lower, about 450 psig or lower, about 500 psig or lower, or within any value encompassed by these endpoints.

The vapor mixture may be fed to a reactor system containing a catalyst. Suitable catalysts may include activated carbons such as NORIT ROX 0.8 and silicon carbide, such as SiC1-E3-M. Preferably the catalyst is commercially available.

3. Removal of Sulfur Dioxide ($SO_2$) Following Formation of Trifluoroacetyl Iodide (TFAI)

During the reaction to form trifluoroacetyl iodide, sulfur dioxide ($SO_2$) in the trifluoroacetyl chloride (TFAC) feed stream may contribute to undesired side reactions. Furthermore, in a continuous process, small amounts of sulfur dioxide ($SO_2$) entering the reactor may build up downstream of the reactor. Without wishing to be bound by theory, it is believed that reactions between the sulfur dioxide ($SO_2$) and hydrogen iodide (HI) may result in the formation of byproducts such as iodine ($I_2$), as well as sulfur-containing byproducts such as dihydrogen sulfide ($H_2S$) and sulfur. Both iodine ($I_2$) and sulfur may form solids, causing equipment difficulties such as plugging in process lines. Furthermore, sulfur-containing species may poison catalysts used in the synthesis process, resulting in a lessening of catalytic activity. It has been found that even small amounts of sulfur dioxide ($SO_2$) in the reactor may promote formation of iodine ($I_2$), leading to plugging of process lines.

Either in combination with removal of sulfur dioxide ($SO_2$) upstream of the reactor or alone, the sulfur dioxide ($SO_2$) may be removed downstream of the reactor by contacting the product stream with one or more solid adsorbents, such as a carbon bed. Suitable solid adsorbents may include those described above in section 1, such as molecular sieves, such as 3 Å molecular sieves available from Acros Organics (also available from Honeywell UOP); 4 Å and XH-9 molecular sieves available from Honeywell UOP, 10 Å molecular sieves available from Grace Davison, and carbon molecular sieves, such as JEChem MSC-3K 172 carbon molecular sieves available from Osaka Gas Chemicals; activated alumina, such as SAS40 ⅛" Alumina available from BASF; zeolite ammonium powders, such as CBV5524G CY available from Zeolyst International; and activated charcoal, such as NORIT ROX 0.8 Activated Carbon available from Cabot, for example.

Figure 11:
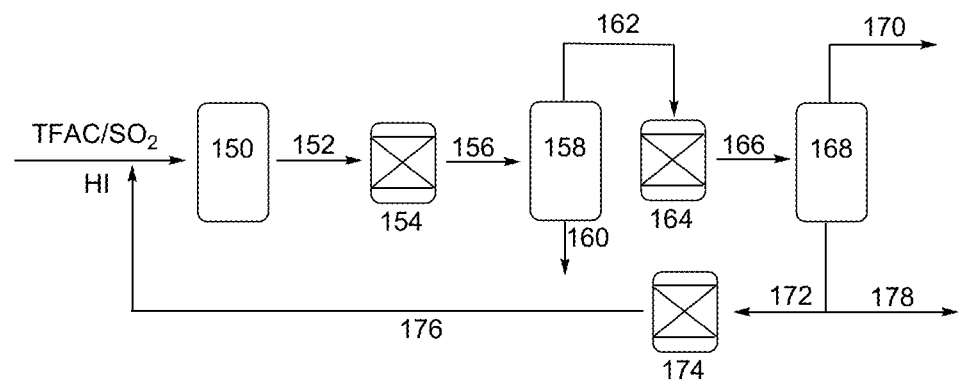
FIG. 11 shows a schematic of a system to remove sulfur dioxide ($SO_2$) corresponding to Examples 11-17.

As shown in FIG. 11, a feed stream comprising trifluoroacetyl chloride (TFAC), sulfur dioxide ($SO_2$), and hydrogen iodide (HI) may be conveyed to a reactor 150. The crude product stream 152 may be conveyed to a first adsorption column 154. A product stream 156 comprising trifluoroacetyl iodide (TFAI), hydrogen chloride (HCl), trifluoroacetyl chloride (TFAC), sulfur dioxide ($SO_2$), and hydrogen iodide (HI) may be conveyed to a first distillation column 158. The bottoms product 160 comprising purified trifluoroacetyl iodide (TFAI) may be removed. The overhead product 162 comprising hydrogen chloride (HCl), trifluoroacetyl chloride (TFAC), hydrogen iodide (HI), and a reduced amount of sulfur dioxide ($SO_2$), may be conveyed to a second adsorption column 164 to provide a product stream 166 comprising hydrogen chloride (HCl), trifluoroacetyl chloride (TFAC), hydrogen iodide (HI), and a reduced amount of sulfur dioxide ($SO_2$). The product stream 166 to a second distillation column 168. The overhead product 170 comprising hydrogen chloride (HCl) may be vented, and the bottoms product 172 comprising trifluoroacetyl chloride (TFAC), hydrogen iodide (HI) and a reduced amount of sulfur dioxide ($SO_2$) may be conveyed to a third adsorption column 174 to provide a recycle stream 176 comprising trifluoroacetyl chloride (TFAC), hydrogen iodide (HI) and a reduced amount of sulfur dioxide ($SO_2$). The trifluoroacetyl chloride (TFAC) 176 may then be recycled back to reactor 150. Alternatively or additionally, a part of the bottoms product stream 172 may be redirected to a purge stream 178.

The starting concentration of sulfur dioxide ($SO_2$) in the trifluoroacetyl chloride (TFAC) may be about 5000 ppm or less, about 2500 ppm or less, about 1000 ppm or less, about 900 ppm or less, about 800 ppm or greater, about 700 ppm or greater, about 600 ppm or greater, about 500 ppm or greater, or any value encompassed by these endpoints, as determined in relation to trifluoroacetyl chloride (TFAC).

The concentration of sulfur dioxide ($SO_2$) in the trifluoroacetyl chloride (TFAC) feed stream may be about 250 ppm or less, about 225 ppm or less, about 200 ppm or less, about 150 ppm or less, about 100 ppm or less, about 50 ppm or less, about 20 ppm or less, about 10 ppm or less, about 5 ppm or less, or about 1 ppm or less.

In the method described above, all of the adsorption columns may be included, two of the adsorption columns may be included, or one of the adsorption columns may be included. The adsorption columns may be placed in any or all of the locations shown in FIG. 11 so as to reduce the sulfur dioxide ($SO_2$) content in the system, thereby reducing the sulfur dioxide ($SO_2$) content in the feed to the reactor. Likewise, the adsorption columns shown in FIG. 11 may be used in conjunction with removal of sulfur dioxide ($SO_2$) from TFAC as shown in FIGS. 1-6.

Referring to FIG. 11, adsorption columns 154, 164, and 174 may be used. Alternatively, only adsorption columns 154 and 164, only adsorption columns 154 and 174, or only adsorption columns 164 and 174 may be used. As a further alternative, only adsorption column 154, only adsorption column 164, or only adsorption column 174 may be used.

Placing the adsorption column at the bottom of the second distillation column (174 in FIG. 11) may be particularly advantageous. At this point in the process, crude trifluoroacetyl iodide (TFAI) and hydrogen chloride (HCl) have already been removed. Furthermore, at this point the sulfur dioxide ($SO_2$) may be more concentrated with respect to trifluoroacetyl chloride (TFAC) as some of the trifluoroacetyl chloride (TFAC) will have undergone the reaction to form trifluoroacetyl iodide (TFAI). Finally, at this point in the process, it may not be necessary to reduce the sulfur dioxide ($SO_2$) concentration in the trifluoroacetyl chloride (TFAC) feed stream towards zero, as sulfur dioxide ($SO_2$) may be removed from the recycle stream.

Once the adsorption column or beds are saturated with sulfur dioxide ($SO_2$), they may be regenerated as described above in section 1.

In addition to the adsorption column or beds, an optional purge may be used to lessen the amount of sulfur dioxide ($SO_2$) present, as described above. The product stream exiting the columns and adsorption column or beds may contain a small amount of sulfur dioxide ($SO_2$), in addition to trifluoroacetyl chloride (TFAC). If desired, the product stream may be periodically purged to remove sulfur dioxide ($SO_2$) from the system, with the loss of only a small amount of trifluoroacetyl chloride (TFAC).

As an alternative, a fresh trifluoroacetyl chloride (TFAC) supply with sulfur dioxide ($SO_2$) impurities may be pre-distilled and treated with adsorbent as described above before being combined with a trifluoroacetyl chloride (TFAC) recycle stream. In this method, the level of sulfur dioxide ($SO_2$) may be low before combining with the recycle stream. Specifically, the level of sulfur dioxide may be about 40 ppm or less, about 30 ppm or less, about 20 ppm or less, about 15 ppm or less, about 10 ppm or less, about 5 ppm or less, or about 1 ppm or less.

4. Alternative Synthesis of TFAI Followed by Removal of $SO_2$ by Distillation

The present disclosure provides a method of synthesizing trifluoroacetyl chloride (TFAI) from trifluoroacetyl chloride (TFAC) and hydrogen iodide (HI) while minimizing the undesired impurities and byproducts described above. In this method, a feed stream comprising trifluoroacetyl chloride (TFAC) with reduced levels of impurities is contacted with a feed stream comprising hydrogen iodide (HI) with reduced levels of impurities. Thus, both the separate feed streams and the combined stream are substantially free of impurities such as sulfur dioxide ($SO_2$), iodine ($I_2$), and ionic metals.

The feed streams may comprise non-recycled (fresh) trifluoroacetyl chloride (TFAC) and hydrogen iodide (HI). Alternatively, the feed streams may comprise recycled trifluoroacetyl chloride (TFAC) and hydrogen iodide (HI). As yet another alternative, the feed streams may comprise a combination of recycled and non-recycled trifluoroacetyl chloride (TFAC) and hydrogen iodide (HI).

The amount of sulfur dioxide ($SO_2$) present in the trifluoroacetyl chloride (TFAC) feed stream may be reduced using simple distillation, azeotropic distillation, and/or contact with a solid adsorbent, for example. The feed streams comprising fresh trifluoroacetyl chloride (TFAC) may be purified, the feed streams comprising recycled trifluoroacetyl chloride (TFAC) may be purified, or both.

The amount of sulfur dioxide ($SO_2$) present in the trifluoroacetyl chloride (TFAC) feed stream may be less than about 400 ppm or less, about 300 ppm or less, about 200 ppm or less, about 100 ppm or less, about 50 ppm or less, about 20 ppm or less, or about 10 ppm or less by weight, as determined by GC-TCD (gas chromatography-thermal conductivity detector).

The feed streams comprising fresh hydrogen iodide (HI) may be purified, the feed streams comprising recycled hydrogen iodide (HI) may be purified, or both. The amount of iodine ($I_2$) present in the hydrogen iodide (HI) feed stream may be reduced using simple distillation and/or contact with a solid adsorbent, for example.

The method of the present disclosure provides a method of producing trifluoroacetyl iodide (TFAI) wherein the amount of iodine ($I_2$) present in the hydrogen iodide (HI) feed stream is less than about 1000 ppm, less than about 500 ppm, less than about 250 ppm, less than about 100 ppm, less than about 50 ppm, less than about 20 ppm, or less than about 10 ppm by weight.

In order to limit some impurities, the molar ratio of trifluoroacetyl chloride (TFAC) to hydrogen iodide (HI) may be about 1:1 or less, about 0.9:1 or less, about 0.8:1 or less, about 0.7:1 or less, or about 0.6:1 or less, or about 0.1:1 or less, or about 0.05:1 or less, or about 0.02:1 or less.

Without wishing to be bound by theory, a ratio of trifluoroacetyl chloride (TFAC) to hydrogen iodide (HI) of 1:2 or less may permit essentially complete reaction of trifluoroacetyl chloride, leaving a product stream comprising sulfur dioxide ($SO_2$) with small amounts of trifluoroacetyl chloride (TFAC), reducing the need to remove residual trifluoroacetyl chloride (TFAC).

Figure 12:
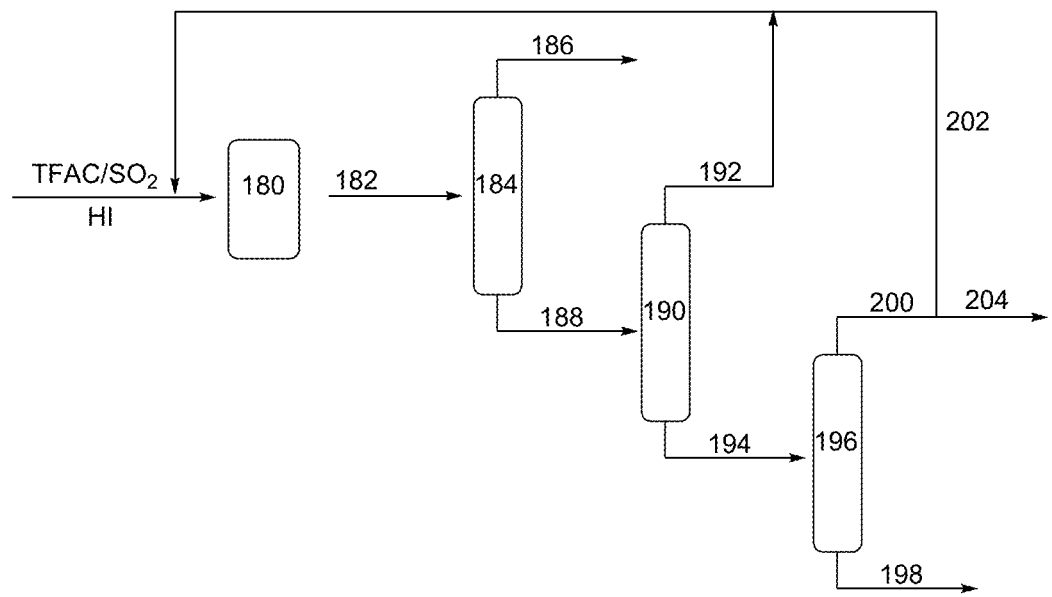
FIG. 12 shows a schematic of a system to remove sulfur dioxide ($SO_2$) corresponding to Example 18.

Sulfur dioxide ($SO_2$) may be then removed from the downstream of the reactor, as shown in FIG. 12. A feed stream comprising trifluoroacetyl chloride (TFAC), sulfur dioxide ($SO_2$) impurities, and hydrogen iodide (HI) in a ratio of 1:2 or less may be conveyed to a reactor 180 to provide a crude product stream 182 comprising trifluoroacetyl iodide (TFAI), hydrogen chloride (HCl), hydrogen iodide (HI), minor amounts of unreacted trifluoroacetyl chloride (TFAC), and sulfur dioxide ($SO_2$). The crude product stream may be conveyed to a first distillation column 184. An overhead product 186 comprising hydrogen chloride (HCl) may be removed. A bottoms product 188 comprising trifluoroacetyl iodide (TFAI), hydrogen iodide (HI), minor amounts of unreacted trifluoroacetyl chloride (TFAC), and sulfur dioxide ($SO_2$) may be conveyed to a second distillation column 190. An overhead product 192 comprising HI may be recycled to the reactor 180. A bottoms product 194 comprising trifluoroacetyl iodide (TFAI), minor amounts of unreacted trifluoroacetyl chloride (TFAC), and sulfur dioxide ($SO_2$) may be conveyed to a third distillation column 196. A bottoms product 198 comprising trifluoroacetyl iodide (TFAI) may be collected as desired. An overhead product 200 comprising trifluoroacetyl chloride (TFAC) and sulfur dioxide ($SO_2$) may be removed from the process as purge stream 204, or a portion of the overhead product 200 may be recycled via stream 202 to the feed stream 182 while the remainder is purged via stream 204.

The following non-limiting Examples serve to illustrate the disclosure.

EXAMPLES

Example 1—PTx Study: 10° C. Isotherm

A set of volume calibrated PTx cells were used to measure azeotrope and azeotrope-like compositions of trifluoroacetyl chloride (TFAC) and sulfur dioxide ($SO_2$). Mixtures of TFAC and $SO_2$ were gravimetrically prepared into evacuated PTx cells; two cells were reserved for measuring each pure component. Once prepared, each of up to eight cells of differing compositions were inserted into a thermostatted chamber. In the chamber, each cell was attached to an instrumentation manifold equipped with calibrated pressure transducers and resistance temperature detectors (RTD); this provided a means to measure and record the total saturation pressure of each cell's contents at its local temperature.

Figure 7:
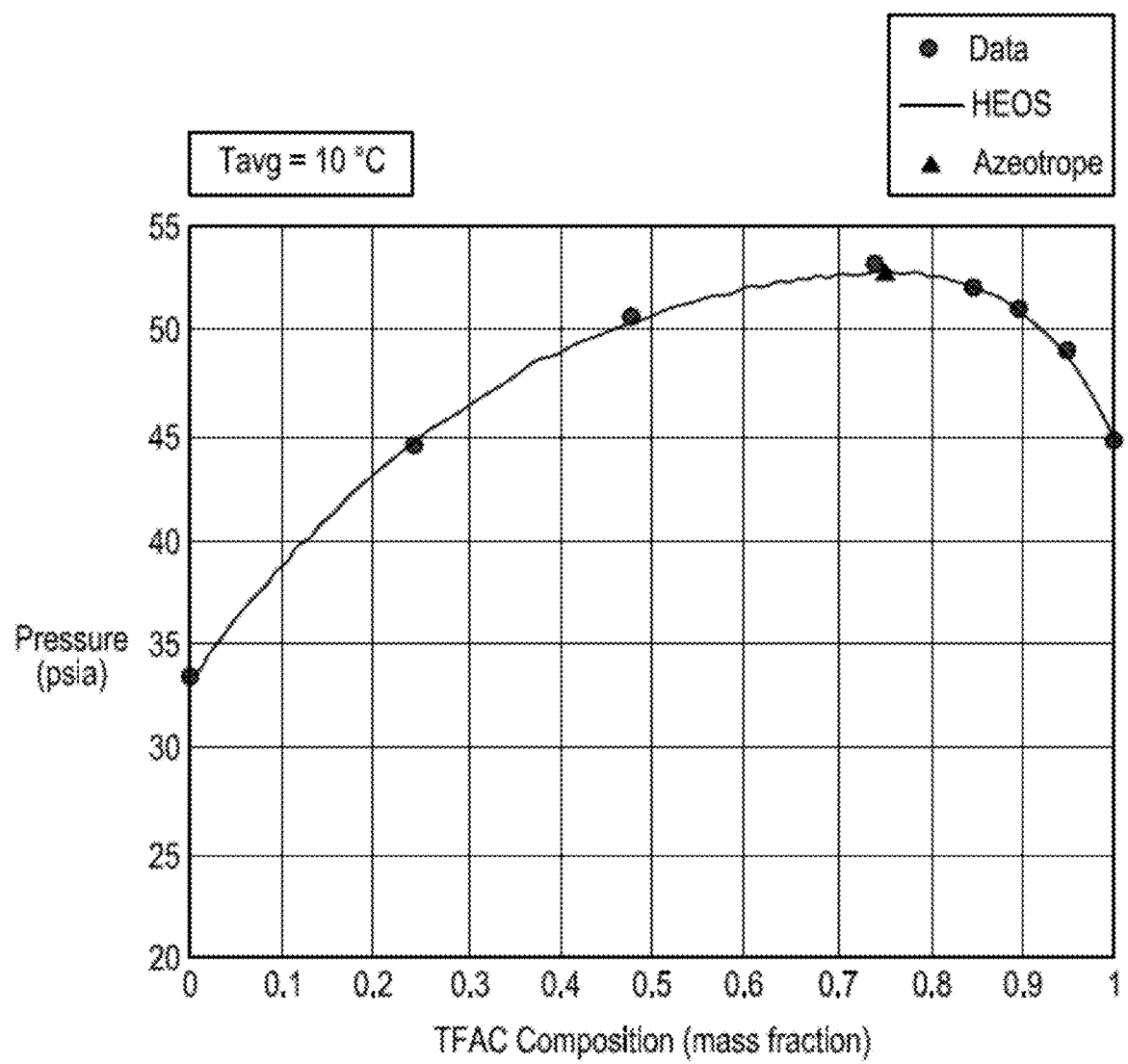
FIG. 7 shows pressure (psia) versus trifluoroacetyl chloride (TFAC) concentration in a PTx Study for TFAC and $SO_2$ at 10° C., corresponding to Example 1.

To establish equilibrium at a target temperature, the set point of the chamber was adjusted to an average temperature ($T_{avg}$) of 10° C. Once at equilibrium, recognized as when temperature and pressures of each cell remain stable for several hours, the local temperature and saturation pressures of each cell were recorded. From these pressure-temperature-composition data, the binary interaction parameters of TFAC and $SO_2$ for the Helmholtz Energy Equation of State (HEOS) were identified. As indicated by the maximum pressure shown in FIG. 7, a minimum boiling azeotrope composition of about 75.0 wt. % TFAC and about 25.0 wt. % $SO_2$ was formed, and data is presented below in Table 1.

TABLE 1

PTx Study for TFAC and SO2 at an average temperature of 10° C.

| TFAC Composition (mass %) | Pressure (psia) |
|---|---|
| 0.0% | 33.4 |
| 24.5% | 44.6 |
| 47.9% | 50.6 |
| 73.8% | 53.2 |
| 84.7% | 52.0 |
| 89.7% | 51.0 |
| 94.9% | 48.9 |
| 100.0% | 44.7 |

Example 2—$SO_2$ Adsorption Efficiency of Various Solid Adsorbents

The adsorption column was charged with about 50 mL of pre-weighed selected solid adsorbent. A 500 mL stainless steel cylinder was charged with about 300 g of 0.1069 wt. % $SO_2$-containing trifluoroacetyl chloride (TFAC). After the system was pressure checked, $SO_2$-containing TFAC was then circulated through the adsorption column by a recirculation pump at room temperature (20° C. to 30° C.). After 24 hours, the recirculation pump was stopped, and a TFAC sample was taken for analysis to determine the concentration of $SO_2$. The $SO_2$ removal efficiency was then calculated.

The tested solid adsorbents are listed below in Table 2.

TABLE 2

| Run # | Adsorbent | Volume of adsorbent, mL | Weight of adsorbent, g |
|---|---|---|---|
| 1 | UOP XH-9 Mol-Sieve | 50 | 42.28 |
| 2 | BASF SAS40 1/8" Alumina | 50 | 36.60 |
| 3 | Zeolyst CBV5524G CY(1.6) | 50 | 30.10 |
| 4 | NORIT ROX0.8 Activated Carbon | 50 | 16.58 |
| 5 | Silica Gel | 50 | 36.13 |
| 6 | Grace Davison 10A Mol-Sieve | 50 | 32.42 |
| 7 | Mol-Sieve 4A (UOP) | 46 | 30.33 |
| 8 | Acros organics 3A Mol-Sieve | 50 | 35.30 |
| 9 | Osaka Gas Chemicals MSC-3K 172 carbon Mol-Sieve | 50 | 32.44 |

Table 3, below, shows the removal efficiency of the different adsorbents. All tested solid adsorbents showed some degree of $SO_2$ removal capacity, with $SO_2$ completely adsorbed by Osaka Gas Chemicals MSC-3K 172 carbon Mol-Sieves.

TABLE 3

| Run # | TFAC used, g | $SO_2$ concentration in TFAC, wt. % Before adsorption | $SO_2$ concentration in TFAC, wt. % After adsorption | $SO_2$ removal, % | g $SO_2$ adsorbed/ 100 g adsorbent |
|---|---|---|---|---|---|
| 1 | 367.14 | 0.1069 | 0.0983 | 8.04 | 0.07 |
| 2 | 329.23 | 0.1069 | 0.0934 | 12.63 | 0.12 |
| 3 | 310.18 | 0.1069 | 0.0922 | 13.75 | 0.15 |
| 4 | 335.46 | 0.1069 | 0.0752 | 29.65 | 0.64 |
| 5 | 319.95 | 0.1069 | 0.0625 | 41.53 | 0.39 |
| 6 | 329.36 | 0.1069 | 0.0509 | 52.39 | 0.57 |
| 7 | 311.35 | 0.1069 | 0.0344 | 67.82 | 0.74 |
| 8 | 332.26 | 0.1069 | 0.0337 | 68.48 | 0.69 |
| 9 | 293.39 | 0.1069 | 0.0000 | 100.00 | 0.97 |

Example 3—$SO_2$ Saturation of Adsorbent

Figure 8:
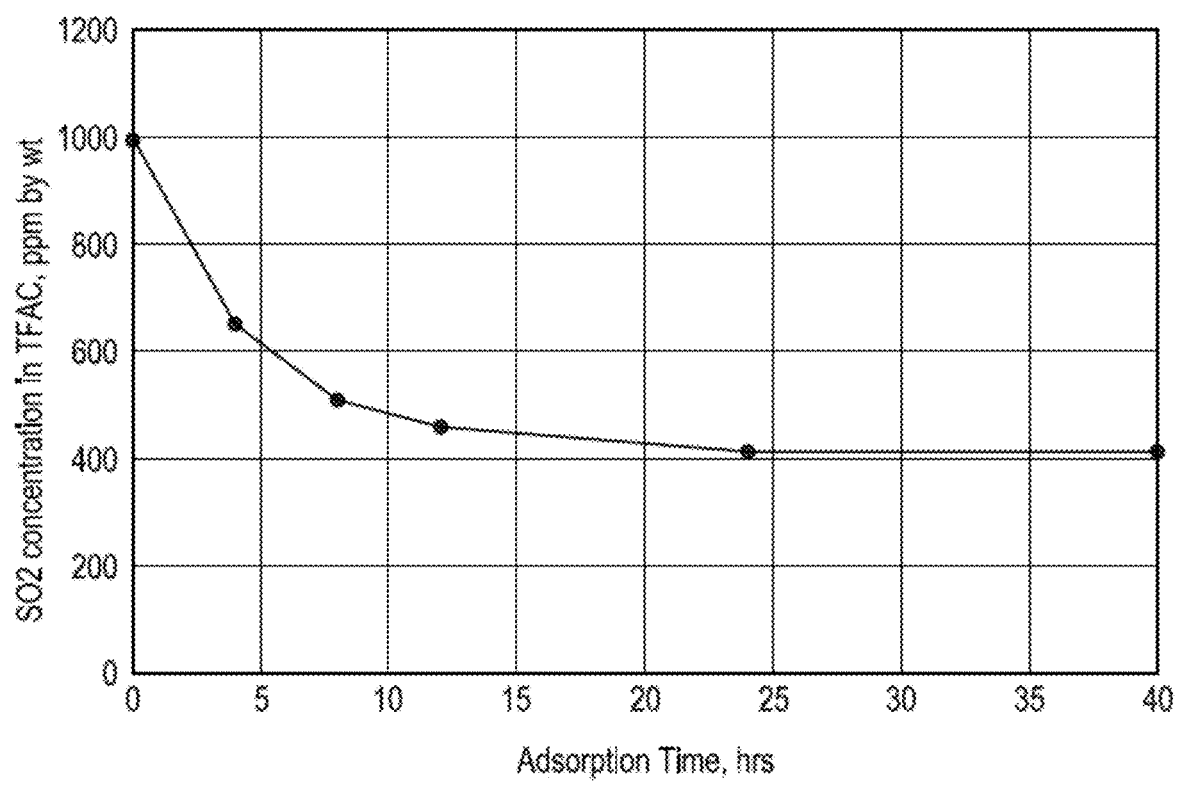
FIG. 8 shows the $SO_2$ concentration in TFAC over time, corresponding to Example 3.

The adsorption column was charged with about 50 mL of Osaka Gas Chemicals MSC-3K 172 carbon Mol-Sieves (29.72 g). A 3-gallon stainless steel cylinder was charged with 5120 g of 0.0995 wt. % $SO_2$-containing TFAC. After the system was pressure checked, the $SO_2$-containing TFAC was circulated through the adsorption column by a recirculation pump at room temperature (20° C. to 30° C.). TFAC samples were taken periodically to analyze $SO_2$ concentration by TCD-GC. The results of the analyses are shown in FIG. 8. After 24 hours, the $SO_2$ concentration in the TFAC was stabilized at 414 ppm, indicating that the adsorbent was saturated by $SO_2$. The $SO_2$ adsorption capacity of this adsorbent was determined to be about 10 wt. % of its weight (or 0.10 g $SO_2$ adsorbed per gram adsorbent).

Example 4—Reduction of $SO_2$ Level in TFAC

This example demonstrates that the $SO_2$ level in trifluoroacetyl chloride (TFAC) feedstock may be reduced to various decreasing levels via multiple cycles of recirculation. Fresh solid adsorbent was used initially and after each successive cycle of recirculation, which was carried out at room temperature (20° C. to 30° C.). As shown in Table 4, the $SO_2$ level was reduced from its original level of 1130 ppm to 258 ppm after Cycle 1; to 156 ppm after Cycle 2; to 80 ppm after Cycle 3; and to zero (below the detection limit of the instrument) after Cycle 4. The percentage of removed $SO_2$ relative to the original amount of $SO_2$ is presented in Table 4 for each cycle.

TABLE 4

| Cycle # | Vol. of adsorbent mL | Wt. of adsorbent g | TFAC used g | $SO_2$ concentration in TFAC, wt. % Before adsorption | $SO_2$ concentration in TFAC, wt. % After adsorption | % $SO_2$ removal* |
|---|---|---|---|---|---|---|
| 1 | 600 | 365.33 | 51529 | 0.113 | 0.0258 | 77.17 |
| 2 | 150 | 91.77 | | 0.0258 | 0.0156 | 86.19 |
| 3 | 150 | 91.56 | | 0.0156 | 0.008 | 92.92 |
| 4 | 450 | 297.18 | | 0.008 | 0.0 | 100.00 |

*Relative to the original $SO_2$ level in the TFAC

Example 5—Regeneration of Spent Adsorbent

Figure 9:
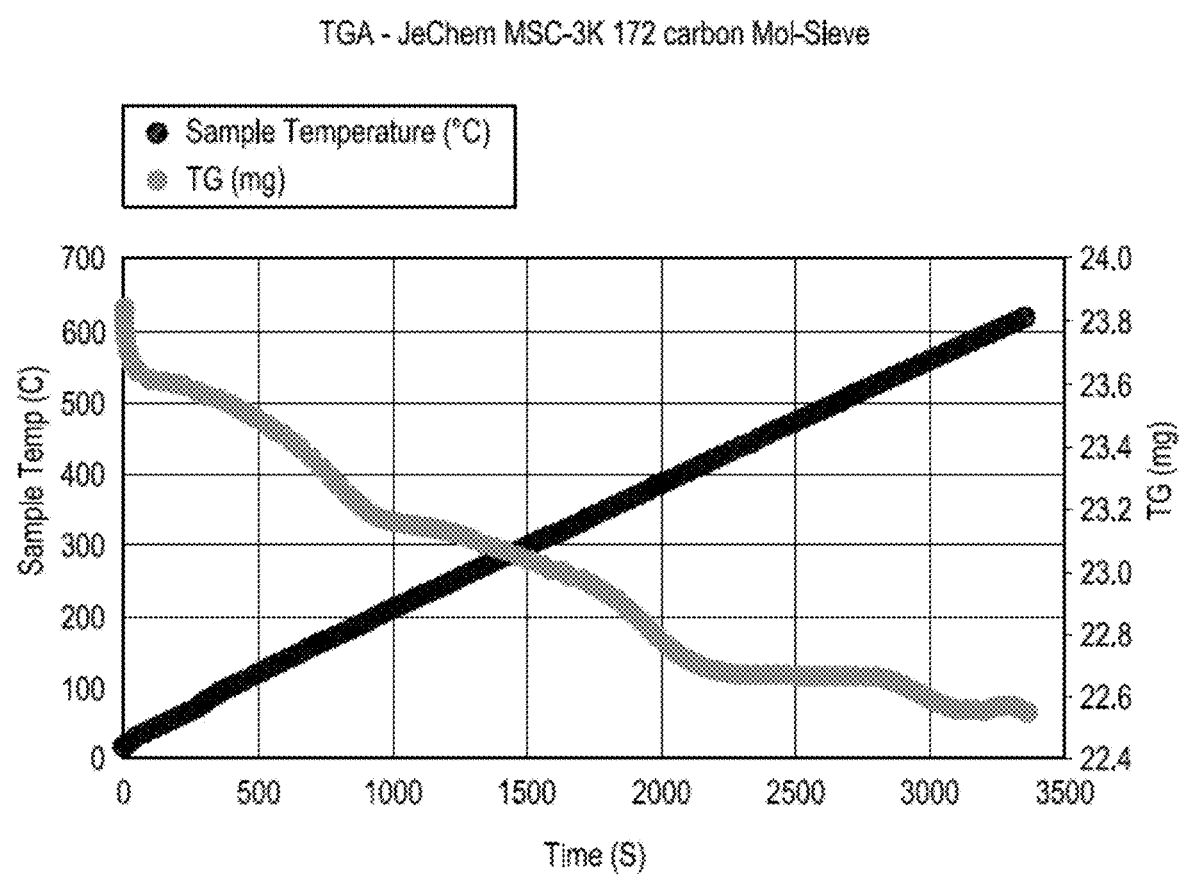
FIG. 9 shows the results of thermogravimetric analysis conducted on spent MSC-3K 172 carbon Mol-Sieves, corresponding to Example 5.
Figure 10:
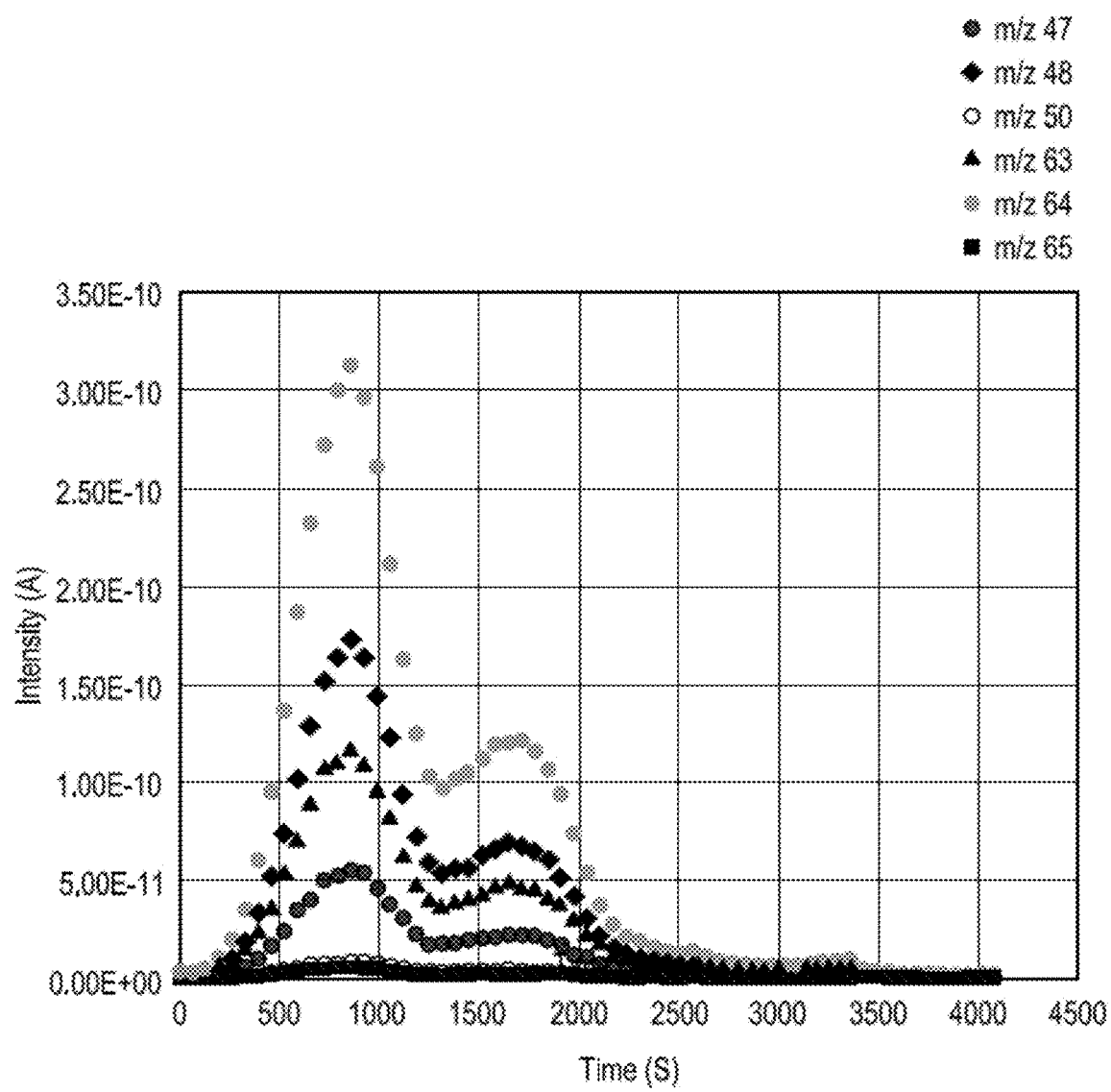
FIG. 10 shows the results of mass spectrometry analysis conducted on spent MSC-3K 172 carbon Mol-Sieves, corresponding to Example 5.

Thermogravimetric analysis/mass spectrometry (TGA-MS) analysis was conducted under nitrogen atmosphere on spent JEChem MSC-3K 172 carbon Mol-Sieves (currently available from Osaka Gas Chemicals) to identify the species adsorbed and the desorption conditions. The TGA results are shown in FIG. 9, and the MS results are shown in FIG. 10.

There were two significant (one major and one minor) weight loss events. Both events were due mainly to $SO_2$ desorption (m/z=64). The major weight loss had a m/z intensity maximum at 920 s, which corresponded to 196° C. on the TGA data. The minor weight loss had a m/z intensity maximum at 1711 s, which corresponds to 335° C. on the TGA data. After 500° C., no m/z values corresponding to $SO_2$ were detected. These results indicate that, at temperatures from 196° C. to 335° C., a partial regeneration of spent adsorbent may be achieved.

Spent JEChem MSC-3K 172 carbon Mol-Sieves were regenerated at 200° C. for 24 hours under nitrogen purge. The regenerated JEChem MSC-3K 172 carbon Mol-Sieves were then used as the adsorbent. The recirculation was conducted at room temperature (20° C. to 30° C.) for 24 hours. As shown in Table 5, after 24 hours recirculation, the $SO_2$ level in the TFAC dropped from 431 ppm to 316 ppm, and its $SO_2$ adsorption capacity was determined to be 0.06 grams $SO_2$ per gram adsorbent (roughly 60% of the capacity of the fresh adsorbent as presented in Example 3). These results indicate that the spent JEChem MSC-3K 172 carbon Mol-Sieve was partially regenerated.

TABLE 5

| Run # | Vol. of adsorbent mL | Wt. of adsorbent g | TFAC used g | $SO_2$ concentration in TFAC, wt. % Before adsorption | $SO_2$ concentration in TFAC, wt. % After adsorption | % $SO_2$ removal | g $SO_2$ adsorbed/g adsorbent |
|---|---|---|---|---|---|---|---|
| 1 | 150 | 100.67 | 53345 | 0.0431 | 0.0316 | 26.68 | 0.06 |

Example 6—Separation and Purification of Trifluoroacetyl Chloride (TFAC)

A composition including crude trifluoroacetyl chloride (TFAC), sulfur dioxide ($SO_2$), and at least one additional impurity is provided. In a first step, the relative amounts of trifluoroacetyl chloride (TFAC) and sulfur dioxide ($SO_2$) are adjusted by adding trifluoroacetyl chloride (TFAC) to the composition, adding sulfur dioxide ($SO_2$) to the composition, or adding both trifluoroacetyl chloride (TFAC) and sulfur dioxide ($SO_2$) to the composition. The composition is then exposed to effective conditions such that an azeotrope or azeotrope-like mixture is formed. The azeotrope or azeotrope-like mixture may then be separated from the at least one impurity by distillation, phase separation, or fractionation. Once the azeotrope or azeotrope-like mixture is separated from the impurity, the components of the azeotrope or azeotrope-like mixture—trifluoroacetyl chloride (TFAC) and sulfur dioxide ($SO_2$)—are separated from one another in a second step. The separation of trifluoroacetyl chloride (TFAC) and sulfur dioxide ($SO_2$) may then be accomplished by distillation, exposure to a solid adsorbent, or a combination thereof.

Example 7—Distillation of Trifluoroacetyl Chloride (TFAC)

A composition including crude trifluoroacetyl chloride (TFAC) and sulfur dioxide ($SO_2$) is provided. The composition is conveyed to a distillation column. The distillate, which may comprise sulfur dioxide ($SO_2$), trifluoroacetyl chloride (TFAC), or a mixture thereof, is collected. The bottoms product, which comprises trifluoroacetyl chloride (TFAC) may be collected. The amount of sulfur dioxide ($SO_2$) present in the bottoms product may be 100 ppm or less, 50 ppm or less, 10 ppm or less, or 1 ppm or less.

Example 8—Azeotropic Distillation of Trifluoroacetyl Chloride (TFAC)

A composition including trifluoroacetyl chloride (TFAC) and 2500 ppm sulfur dioxide ($SO_2$) is purified to provide a purified stream of TFAC containing 5 ppm $SO_2$.

1000 lbs/hr of crude TFAC containing 997.5 lb/hr of TFAC and 2.5 lb/hr $SO_2$ is fed to a distillation column operating at 52.7 psia at the top of the column. The distillation column has 40 stages, and is fitted with a condenser cooled with chilled water with a supply temperature of 5° C. such that the overhead temperature of the column operates at about 10° C. The reboiler is heated with steam (e.g. 10 psig saturated steam at 115° C.). At a reflux rate of 1540 lb/hr and boilup rate of 1820 lb/hr, a bottoms stream of purified TFAC containing 5 ppm $SO_2$ is recovered. The overhead and distillate streams are concentrated to the approximate azeotropic composition of TFAC and $SO_2$ (about 76 wt. % TFAC, total distillate flowrate 10.25 lb/hr). The distillation yield of TFAC is over 99.2%.

TABLE 6

| | Compositions | | |
|---|---|---|---|
| | Feed (wt %) | Distillate (wt %) | Bottoms (wt %) |
| TFAC | 99.75 | 75.66 | 99.999 |
| SO$_2$ | 2.5 | 24.34 | 0.0005 |

TABLE 7

| Column Conditions | |
|---|---|
| Number of stages | 40 |
| Feed Stage | 20 |
| Overhead Pressure | 52.7 psia |
| Overhead Temperature | 10° C. |
| Bottoms Temperature | 14.8° C. |
| Reflux Ratio | 150 |
| Boil up Ratio | 1.84 |

Other conditions, including different number of stages, different feed stage, different pressure, different reflux ratio and different boil up ratio may also be used to purify TFAC/SO2 mixtures.

Example 9—Alternative Method for Distillation of Trifluoroacetyl Chloride (TFAC)

A composition including crude trifluoroacetyl chloride (TFAC) and sulfur dioxide (SO$_2$) is provided. In a first step, the composition is conveyed to a distillation column and exposed to effective conditions such that an azeotrope or azeotrope-like mixture is formed. The bottoms product, which comprises trifluoroacetyl chloride (TFAC) may be collected. The amount of sulfur dioxide (SO$_2$) present in the bottoms product may be 100 ppm or less, 50 ppm or less, 10 ppm or less, or 1 ppm or less.

The azeotrope or azeotrope-like mixture is collected as the distillate. The components of the azeotrope or azeotrope-like mixture in the distillate—trifluoroacetyl chloride (TFAC) and sulfur dioxide (SO$_2$)—are separated from one another in a second step. The separation of trifluoroacetyl chloride (TFAC) and sulfur dioxide (SO$_2$) may then be accomplished by distillation, exposure to a solid adsorbent, or a combination thereof.

Example 10—Purge Method for Sulfur Dioxide (SO$_2$) Removal Following Trifluoroacetyl Iodide (TFAI) Formation (Comparative Example)

This comparative example illustrates removing a portion of SO$_2$ from a recycle stream to control SO$_2$ buildup in the process without the use of an adsorption column in the recycle. A feed stream comprising 999 lb/hr of TFAC and 1 lb/hr SO$_2$ (1000 ppm SO$_2$ with respect to TFAC) is preconditioned to remove SO$_2$ by methods described previously (one or both of distillation and adsorption "upstream") for a composition comprising 50 ppm SO$_2$ with respect to TFAC (i.e. mass ratio of TFAC/SO$_2$ of about 20000/1). This stream is combined with HI (which may contain impurities) and a recycle stream comprising TFAC and HI (which may contain other impurities, including SO$_2$). The combined streams are fed to a reactor. Sulfur dioxide (SO$_2$) is not consumed in the reactor and may therefore become concentrated during the process. The reactor effluent is fed to a first distillation column to recover a bottoms stream comprising TFAI. The overhead of the first distillation column is fed to a second distillation column. A stream comprising HCl will be recovered in the overhead of the second distillation column. The bottoms of the second distillation column comprising TFAC, HI and SO$_2$ is recycled to the reactor. To control the build-up of SO$_2$, a portion of the recycle stream is purged (i.e. removed from the recycle stream). To maintain the desired level of 250 ppm SO$_2$ in the recycle stream, approximately 15% of the recycle stream must be purged, representing a yield loss for the reactants TFAC and HI. The result of this purge is the loss of approximately 6% of the fresh incoming TFAC (63×0.9435). Additional losses of TFAC during SO$_2$ removal via distillation may occur.

TABLE 8

| | Purge stream composition | | | |
|---|---|---|---|---|
| Component | 2nd Column bottoms (lb/hr) | TFAC recycle (lb/hr) | Purge (lb/hr) | Composition (wt. %) |
| HI | 22.57 | 19.19 | 3.38 | 5.37% |
| TFAC | 396.87 | 337.46 | 59.41 | 94.35% |
| SO$_2$ | 0.33 | 0.28 | 0.05 | 0.08% |
| Others | 0.86 | 0.73 | 0.13 | 0.21% |
| Total | 420.6 | 357.7 | 63.0 | |

Example 11: Removal of Sulfur Dioxide (SO$_2$) Following Trifluoroacetyl Iodide (TFAI) Formation Using One Adsorption Column A feed stream comprising trifluoroacetyl chloride (TFAC), sulfur dioxide (SO$_2$), and hydrogen iodide (HI) is conveyed to a reactor. The crude product stream is conveyed to a first adsorption column, shown as 154 in FIG. 11, to provide a product stream comprising trifluoroacetyl iodide (TFAI), hydrogen chloride (HCl), trifluoroacetyl chloride (TFAC), and hydrogen iodide (HI). This product stream is then conveyed to a first distillation column. The bottoms product of the first distillation column comprises purified trifluoroacetyl iodide (TFAI). The overhead product comprises hydrogen chloride, trifluoroacetyl chloride (TFAC), and hydrogen iodide (HI). This stream is passed through a compressor prior to being conveyed to a second distillation column. The overhead product of the second distillation column, comprising hydrogen chloride (HCl) is vented, and the bottoms product, comprising trifluoroacetyl chloride (TFAC) and hydrogen iodide (HI) is then recycled back to the feed stream.

Example 12: Removal of Sulfur Dioxide (SO$_2$) Following Trifluoroacetyl Iodide (TFAI) Formation Using One Adsorption Column A feed stream comprising trifluoroacetyl chloride (TFAC), sulfur dioxide (SO$_2$), and hydrogen iodide (HI) is conveyed to a reactor. The crude product stream comprising trifluoroacetyl iodide (TFAI), sulfur dioxide (SO$_2$), hydrogen chloride (HCl), trifluoroacetyl chloride (TFAC), and hydrogen iodide (HI) may be conveyed to a first distillation column, from which the bottoms product comprising purified trifluoroacetyl iodide (TFAI) may be removed. The overhead product comprising hydrogen chloride (HCl), sulfur dioxide (SO$_2$), trifluoroacetyl chloride (TFAC), and hydrogen iodide (HI) is conveyed to an adsorption column (164 in FIG. 11) to provide a product stream with a reduced amount of sulfur dioxide ($SO_2$). The product stream is then passed through a compressor prior to being conveyed to a second distillation column. The overhead product of the second distillation column comprising hydrogen chloride (HCl) is vented, and the bottoms product, comprising trifluoroacetyl chloride (TFAC) and hydrogen iodide (HI) is then recycled back to the feed stream.

Example 13: Removal of Sulfur Dioxide ($SO_2$) Following Trifluoroacetyl Iodide (TFAI) Formation Using One Adsorption Column A feed stream comprising 999 lb/hr of TFAC and 1 lb/hr $SO_2$ (1000 ppm $SO_2$ with respect to TFAC) is preconditioned to remove $SO_2$ by methods described previously (one or both of distillation and adsorption "upstream") for a composition comprising 50 ppm $SO_2$ with respect to TFAC (i.e. mass ratio of TFAC/SO2 of about 20000/1). This stream is combined with HI (which may contain impurities) and a recycle stream comprising TFAC and HI (which may contain other impurities, including $SO_2$). The combined streams are fed to a reactor. Sulfur dioxide ($SO_2$) is not consumed in the reactor and may therefore become concentrated during the process. The reactor effluent is fed to a first distillation column to recover a bottoms stream comprising TFAI. The overhead of the first distillation column comprising hydrogen chloride (HCl), sulfur dioxide ($SO_2$), trifluoroacetyl chloride (TFAC), and hydrogen iodide (HI) is conveyed to a second distillation column. A stream comprising HCl is recovered in the overhead of the second distillation column. The bottoms of the second distillation column comprising trifluoroacetyl chloride (TFAC), hydrogen iodide (HI) and sulfur dioxide ($SO_2$) is conveyed to an adsorption column (174 in FIG. 11) to provide a product stream comprising trifluoroacetyl chloride (TFAC) and hydrogen iodide (HI) with a reduced concentration of sulfur dioxide ($SO_2$). The trifluoroacetyl chloride (TFAC) and hydrogen iodide (HI) may then be recycled.

The adsorption column is packed with an adsorbent, for example JEChem MSC-3K 172 carbon molecular sieves available from Osaka Gas Chemicals. To maintain the desired level of 250 ppm $SO_2$ in the recycle stream, a purge from the recycle stream is not required because of the adsorbent's capability to adsorb $SO_2$ selectively from the recycle stream. Hence, the yield loss associated with a purge is eliminated. The composition of the recycle stream is shown in Table 9 below, based on a 999 lb/hr TFAC feed rate, a 98% conversion of TFAC per pass and mol ratio of TFAC/HI of 1.4 at the reactor inlet. Additional losses of TFAC during $SO_2$ removal via distillation is not shown.

TABLE 9

| | Recycle stream composition | | |
|---|---|---|---|
| Component | 2nd Column bottoms (lb/hr) | TFAC recycle (lb/hr) | $SO_2$ Adsorbed (lb/hr) |
| HI | 23.65 | 23.65 | — |
| TFAC | 419.90 | 419.90 | — |
| $SO_2$ | 0.35 | 0.31 | 0.04 |
| Others | 5.98 | 5.98 | — |
| Total | 449.88 | 449.83 | 0.04 |

Example 14: Removal of Sulfur Dioxide ($SO_2$) Following Trifluoroacetyl Iodide (TFAI) Formation Using Two Adsorption Columns A feed stream comprising trifluoroacetyl chloride (TFAC), sulfur dioxide ($SO_2$), and hydrogen iodide (HI) is conveyed to a reactor. The crude product stream comprising trifluoroacetyl iodide (TFAI), sulfur dioxide ($SO_2$), hydrogen chloride (HCl), trifluoroacetyl chloride (TFAC), and hydrogen iodide (HI) is conveyed to a first adsorption column (154 in FIG. 11). A product stream comprising trifluoroacetyl iodide (TFAI), hydrogen chloride (HCl), trifluoroacetyl chloride (TFAC), hydrogen iodide (HI) and a reduced amount of sulfur dioxide ($SO_2$) is then conveyed to a first distillation column. The bottoms product comprising purified trifluoroacetyl iodide (TFAI) is removed. The overhead product comprising hydrogen chloride (HCl), trifluoroacetyl chloride (TFAC), sulfur dioxide ($SO_2$) and hydrogen iodide (HI) is conveyed to a second adsorption column (164 of FIG. 11) to provide a product stream comprising hydrogen chloride (HCl), trifluoroacetyl chloride (TFAC), hydrogen iodide (HI) and a reduced amount of sulfur dioxide ($SO_2$) and passed through a compressor prior to being conveyed to a second distillation column. The overhead product comprising hydrogen chloride (HCl) may be vented, and the bottoms product comprising trifluoroacetyl chloride (TFAC), hydrogen iodide (HI) and a reduced concentration of sulfur dioxide ($SO_2$) may be recycled.

Example 15: Removal of Sulfur Dioxide ($SO_2$) Following Trifluoroacetyl Iodide (TFAI) Formation Using Two Adsorption Columns A feed stream comprising trifluoroacetyl chloride (TFAC), sulfur dioxide ($SO_2$), and hydrogen iodide (HI) is conveyed to a reactor. The crude product stream comprising trifluoroacetyl iodide (TFAI), sulfur dioxide ($SO_2$), hydrogen chloride (HCl), trifluoroacetyl chloride (TFAC), and hydrogen iodide (HI) is conveyed to a first adsorption column (154 in FIG. 11). A product stream comprising trifluoroacetyl iodide (TFAI), hydrogen chloride (HCl), trifluoroacetyl chloride (TFAC), hydrogen iodide (HI) and a reduced amount of sulfur dioxide ($SO_2$) is then conveyed to a first distillation column. The bottoms product comprising purified trifluoroacetyl iodide (TFAI) is removed. The overhead product comprising hydrogen chloride (HCl), trifluoroacetyl chloride (TFAC), sulfur dioxide ($SO_2$) and hydrogen iodide (HI) is passed through a compressor prior to being conveyed to a second distillation column. The overhead product comprising hydrogen chloride (HCl) may be vented, and the bottoms product comprising trifluoroacetyl chloride (TFAC), hydrogen iodide (HI) and sulfur dioxide ($SO_2$) is passed to a second adsorption column (174 of FIG. 11) to provide a product stream comprising trifluoroacetyl chloride (TFAC) and hydrogen iodide (HI) with a reduced concentration of sulfur dioxide ($SO_2$). The trifluoroacetyl chloride (TFAC) and hydrogen iodide (HI) may then be recycled.

Example 16: Removal of Sulfur Dioxide ($SO_2$) Following Trifluoroacetyl Iodide (TFAI) Formation Using Two Adsorption Columns A feed stream comprising trifluoroacetyl chloride (TFAC), sulfur dioxide ($SO_2$), and hydrogen iodide (HI) is conveyed to a reactor. The crude product stream comprising trifluoroacetyl iodide (TFAI), sulfur dioxide ($SO_2$), hydrogen chloride (HCl), trifluoroacetyl chloride (TFAC), and hydrogen iodide (HI) is conveyed to a first distillation column. The bottoms product comprising purified trifluoroacetyl iodide (TFAI) may be removed. The overhead product comprising hydrogen chloride (HCl), trifluoroacetyl chloride (TFAC), sulfur dioxide ($SO_2$), and hydrogen iodide (HI) may be conveyed to a first adsorption column (164 of FIG. 11) to provide a product stream comprising hydrogen chloride (HCl), trifluoroacetyl chloride (TFAC), hydrogen iodide (HI), and a reduced amount of sulfur dioxide ($SO_2$) and passed through a compressor prior to being conveyed to a second distillation column. The overhead product comprising hydrogen chloride (HCl) may be vented, and the bottoms product comprising trifluoroacetyl chloride (TFAC), hydrogen iodide (HI) and sulfur dioxide ($SO_2$) is conveyed to a second adsorption column (174 of FIG. 11) to provide a product stream comprising trifluoroacetyl chloride (TFAC) and hydrogen iodide (HI) with a reduced concentration of sulfur dioxide ($SO_2$). The trifluoroacetyl chloride (TFAC) and hydrogen iodide (HI) is then recycled.

Example 17: Removal of Sulfur Dioxide ($SO_2$) Following Trifluoroacetyl Iodide (TFAI) Formation Using Three Adsorption Columns A feed stream comprising trifluoroacetyl chloride (TFAC), sulfur dioxide ($SO_2$), and hydrogen iodide (HI) is conveyed to a reactor. The crude product stream comprising trifluoroacetyl iodide (TFAI), sulfur dioxide ($SO_2$), hydrogen chloride (HCl), trifluoroacetyl chloride (TFAC), and hydrogen iodide (HI) is conveyed to a first adsorption column (154 of FIG. 11) to provide a product stream comprising trifluoroacetyl iodide (TFAI), hydrogen chloride (HCl), trifluoroacetyl chloride (TFAC), hydrogen iodide (HI), and a reduced amount of sulfur dioxide ($SO_2$). The product stream is conveyed to a first distillation column. The bottoms product comprising purified trifluoroacetyl iodide (TFAI) may be removed. The overhead product comprising hydrogen chloride (HCl), trifluoroacetyl chloride (TFAC), sulfur dioxide ($SO_2$), and hydrogen iodide (HI) may be conveyed to a first adsorption column (164 of FIG. 11) to provide a product stream comprising hydrogen chloride (HCl), trifluoroacetyl chloride (TFAC), hydrogen iodide (HI), and a reduced amount of sulfur dioxide ($SO_2$) and passed through a compressor prior to being conveyed to a second distillation column. The overhead product comprising hydrogen chloride (HCl) may be vented, and the bottoms product comprising trifluoroacetyl chloride (TFAC), hydrogen iodide (HI) and sulfur dioxide ($SO_2$) is conveyed to a second adsorption column (174 of FIG. 11) to provide a product stream comprising trifluoroacetyl chloride (TFAC) and hydrogen iodide (HI) with a reduced concentration of sulfur dioxide ($SO_2$). The trifluoroacetyl chloride (TFAC) and hydrogen iodide (HI) is then recycled.

Example 18: Alternative Synthesis of Trifluoroacetyl Iodide (TFAI) and Removal of Sulfur Dioxide ($SO_2$)

A feed stream comprising 500 lb/hr trifluoroacetyl chloride (TFAC) and 0.125 lb/hr sulfur dioxide ($SO_2$) (250 ppm with respect to TFAC) is contacted with a feed stream comprising fresh and recycle hydrogen iodide (HI). The fresh HI may contain iodine ($I_2$) in an amount of 1000 ppm or less with respect to HI. The combined stream of fresh and recycle hydrogen iodide (HI) comprises 1932 lb/hr HI and 0.15 lb/hr iodine ($I_2$) resulting in a mole ratio of trifluoroacetyl chloride (TFAC) to hydrogen iodide (HI) of 0.25:1. The feed streams are conveyed to a reactor to provide a crude product stream comprising trifluoroacetyl iodide (TFAI), hydrogen chloride (HCl), hydrogen iodide (HI), trifluoroacetyl chloride (TFAC), and sulfur dioxide ($SO_2$). The crude product stream is conveyed to a first distillation column. An overhead product comprising hydrogen chloride (HCl) is removed. A bottoms product comprising trifluoroacetyl iodide (TFAI), hydrogen iodide (HI), trifluoroacetyl chloride (TFAC), and sulfur dioxide ($SO_2$) is then conveyed to a second distillation column. The overhead product comprising hydrogen iodide is recycled to the reactor. The bottoms product comprising trifluoroacetyl iodide (TFAI), trifluoroacetyl chloride (TFAC), and sulfur dioxide ($SO_2$) is conveyed to a third distillation column. The bottoms product comprising purified trifluoroacetyl iodide (TFAI) is collected, while the overhead product comprising trifluoroacetyl chloride (TFAC) and sulfur dioxide ($SO_2$) is purged. Optionally a portion of this stream may be recycled. FIG. 12 shows a schematic of the process. Tables 10 and 11 below show a material balance.

TABLE 10

| Reactant | Fresh Feed (lb/hr) | Feed to Reactor (lb/hr) | Reactor Crude (lb/hr) |
|---|---|---|---|
| Stream No. in FIG. 12 | | | 182 |
| HCl | | | 136.32 |
| HI | 477.696 | 1930.083 | 1452.39 |
| TFAC | 499.875 | 499.875 | 5.00 |
| $SO_2$ | 0.125 | 0.125 | 0.125 |
| TFAI | | | 836.25 |
| $I_2$ | 0.421 | 0.421 | 0.421 |
| Total | 978.12 | 2430.50 | 2430.50 |

TABLE 11

| Reactant | 1st Column Top (lb/hr) | 1st Column Bottom (lb/hr) | 2nd Column Top (lb/hr) | 2nd Column Bottom (lb/hr) | 3rd Column Top (lb/hr) | 3rd Column Bottom (lb/hr) | Purge (lb/hr) |
|---|---|---|---|---|---|---|---|
| Stream No. FIG. 12 | 186 | 188 | 192 | 194 | 200 | 198 | 204 |
| HCl | 136.32 | | | | | | |
| HI | | 1452.39 | 1452.39 | | | | |
| TFAC | | 5.00 | | 5.00 | 5.00 | | 5.00 |
| $SO_2$ | | 0.125 | | 0.125 | 0.125 | | 0.125 |

TABLE 11-continued

| Reactant | 1st Column Top (lb/hr) | 1st Column Bottom (lb/hr) | 2nd Column Top (lb/hr) | 2nd Column Bottom (lb/hr) | 3rd Column Top (lb/hr) | 3rd Column Bottom (lb/hr) | Purge (lb/hr) |
|---|---|---|---|---|---|---|---|
| TFAI | | 836.25 | | 836.25 | | 836.25 | |
| I2 | | 0.421 | | 0.421 | | 0.421 | |
| Total | 136.32 | 2294.18 | 1452.39 | 841.79 | 5.12 | 836.67 | 5.12 |

Example 19: $SO_2$ Removal from TFAC by Batch Distillation 52.73 lbs of 740 ppm $SO_2$-containing TFAC was charged into a distillation unit equipped with a 10-gallon reboiler, a 2" ID×120" L column (packed with Goodloe 2" dia×6" thick structured metal packing) and a tube in shell condenser (10.45 ft2 of surface area) for a batch distillation to remove $SO_2$ from TFAC. The reboiler was heated up to about 40° C. with 30 psig steam/city water mixture. During the operation, every 2-4 hours, 2-4 psig of column pressure was vented-off to a lights collection cylinder from the column overhead to remove non-condensable gases at the startup and to purge out concentrated $SO_2$ from the system. The overhead reflux and reboiler samples were taken periodically for $SO_2$ analysis using a pre-calibrated TCD-GC. Based on the results, $SO_2$ contained in the TFAC was concentrated into the column overhead. With the overhead purge continued, the reboiler $SO_2$ concentration continued to drop and eventually reached the GC detection limit (less than 5 ppm). After 8 reboiler samples showed below detection limit (<5 ppm) of $SO_2$, the reboiler material was fully drained to a heavies collection cylinder with 49.67 lbs of purified TFAC collected containing <5 ppm $SO_2$ (less than detection limit) representing a yield of 96.84%. The lights collection cylinder gained 1.53 lbs during the operation which gave a total mass balance of 99.82%.

A second batch distillation was conducted in the same distillation unit as described above. 54.70 lbs of 958 ppm $SO_2$-containing TFAC was charged into the reboiler. During the operation, every 2-4 hours, 2-4 psig of column pressure was vented-off to a lights collection cylinder from the column overhead to remove non-condensable gases at the startup and to purge out concentrated $SO_2$ from the system. The overhead reflux and reboiler samples were taken periodically for $SO_2$ analysis using a pre-calibrated TCD-GC. Based on the results, $SO_2$ contained in the TFAC was concentrated into the column overhead stream. With the overhead purge continued, the reboiler $SO_2$ concentration continued to drop and eventually reached the GC detection limit (less than 5 ppm). After 3 reboiler samples showed below detection limit (<5 ppm) of $SO_2$, the reboiler material was fully drained to a heavies collection cylinder with 53.93 lbs of purified TFAC collected containing <5 ppm $SO_2$ (less than detection limit) representing a yield of 98.59%. The lights collection cylinder gained 0.49 lbs during the operation which gave a total mass balance of 99.49%.

Aspects

Aspect 1 is a composition comprising an azeotrope or azeotrope-like composition consisting essentially of effective amounts of trifluoroacetyl chloride (TFAC) and sulfur dioxide ($SO_2$).

Aspect 2 is the composition of Aspect 1, wherein the azeotrope or azeotrope-like composition has a boiling point of about 10.0° C.±3° C. at a pressure of about 45 psia±0.3 psia.

Aspect 3 is the composition of Aspect 1 or Aspect 2, wherein the azeotrope or azeotrope-like composition consists essentially of from about 25 wt. % to about 99 wt. % trifluoroacetyl chloride (TFAC) and from about 1 wt. % to about 75 wt. % sulfur dioxide ($SO_2$).

Aspect 4 is the composition of any of Aspects 1-3, wherein the azeotrope or azeotrope-like composition consists essentially of from about 48 wt. % to about 90 wt. % trifluoroacetyl chloride (TFAC) and from about 10 wt. % to about 52 wt. % sulfur dioxide ($SO_2$).

Aspect 5 is a method of forming an azeotrope or azeotrope-like composition comprising the step of combining trifluoroacetyl chloride (TFAC) and sulfur dioxide ($SO_2$) to form an azeotrope or azeotrope-like composition consisting essentially of trifluoroacetyl chloride (TFAC) and sulfur dioxide ($SO_2$) having a boiling point of about 10.0° C.±3° C. at a pressure of about 45 psia±0.3 psia.

Aspect 6 is the method of Aspect 5, wherein the combining step comprises combining from about 25 wt. % to about 99 wt. % trifluoroacetyl chloride (TFAC) and from about 1 wt. % to about 75 wt. % sulfur dioxide ($SO_2$).

Aspect 7 is a method of removing sulfur dioxide ($SO_2$) from trifluoroacetyl chloride (TFAC), the method comprising at least one of distillation, adsorption, or a combination thereof.

Aspect 8 is the method of Aspect 7, further comprising the steps of: conveying a feed stream to a distillation column, the feed stream comprising trifluoroacetyl chloride (TFAC) and sulfur dioxide ($SO_2$); collecting the distillate from the distillation column, the distillate comprising trifluoroacetyl chloride and sulfur dioxide ($SO_2$); and collecting a bottoms product from the distillation column, the bottoms product consisting essentially of trifluoroacetyl chloride (TFAC).

Aspect 9 is the method of Aspect 7, further comprising the steps of: conveying a feed stream to a distillation column, the feed stream comprising trifluoroacetyl chloride (TFAC) and sulfur dioxide ($SO_2$); forming an azeotrope or azeotrope-like composition consisting essentially of effective amounts of trifluoroacetyl chloride (TFAC) and sulfur dioxide ($SO_2$); collecting the distillate from the distillation column, the distillate comprising the azeotrope or azeotrope-like composition; and collecting a bottoms product from the distillation column, the bottoms product consisting essentially of trifluoroacetyl chloride (TFAC).

Aspect 10 is the method of Aspect 7, further comprising the steps of: conveying a feed to a distillation column, the feed stream comprising trifluoroacetyl chloride (TFAC), sulfur dioxide ($SO_2$); forming an azeotrope or azeotrope-like composition consisting essentially of effective amounts of trifluoroacetyl chloride (TFAC) and sulfur dioxide ($SO_2$); collecting the distillate from the distillation column, the distillate comprising the azeotrope or azeotrope-like composition; collecting a bottoms product from the distillation column; contacting the bottoms product from the distillation column with a solid adsorbent; and collecting a product stream from the solid adsorbent consisting essentially of trifluoroacetyl chloride (TFAC).

Aspect 11 is the method of Aspect 7, further comprising the steps of: conveying a feed stream to a distillation column, the feed stream comprising trifluoroacetyl chloride (TFAC), sulfur dioxide ($SO_2$); forming an azeotrope or azeotrope-like composition consisting essentially of effective amounts of trifluoroacetyl chloride (TFAC) and sulfur dioxide ($SO_2$); collecting a bottoms product from the distillation column; collecting the distillate from the column, the distillate comprising the azeotrope or azeotrope-like composition; contacting the distillate with a solid adsorbent; and collecting a product stream from the solid adsorbent consisting essentially of trifluoroacetyl chloride (TFAC).

Aspect 12 is the method of Aspect 7, further comprising the steps of: conveying a feed stream to a distillation column, the feed stream comprising trifluoroacetyl chloride (TFAC), sulfur dioxide ($SO_2$); forming an azeotrope or azeotrope-like composition consisting essentially of effective amounts of trifluoroacetyl chloride (TFAC) and sulfur dioxide ($SO_2$); collecting a bottoms product from the distillation column; contacting the bottoms product from the distillation column with a first solid adsorbent; collecting from the first solid adsorbent a product stream consisting essentially of trifluoroacetyl chloride (TFAC); collecting a distillate from the column, the distillate comprising the azeotrope or azeotrope-like composition; contacting the distillate from the distillation column with a second solid adsorbent; and collecting from the second solid adsorbent a product stream consisting essentially of trifluoroacetyl chloride (TFAC).

Aspect 13 is the method of Aspect 7, further comprising the steps of: contacting a feed stream with a first solid adsorbent, the feed stream comprising trifluoroacetyl chloride (TFAC) and sulfur dioxide ($SO_2$); collecting from the solid adsorbent a product stream comprising trifluoroacetyl chloride (TFAC) and sulfur dioxide ($SO_2$); conveying the product stream comprising trifluoroacetyl chloride (TFAC) and sulfur dioxide ($SO_2$) to a distillation column; forming an azeotrope or azeotrope-like composition consisting essentially of effective amounts of trifluoroacetyl chloride (TFAC) and sulfur dioxide ($SO_2$); collecting a bottoms product from the distillation column; contacting the bottoms product from the distillation column with a second solid adsorbent; collecting from the second solid adsorbent a product stream consisting essentially of trifluoroacetyl chloride (TFAC); collecting a distillate from the column, the distillate comprising the azeotrope or azeotrope-like composition; contacting the distillate from the distillation column with a third solid adsorbent; and collecting from the third solid adsorbent a product stream consisting essentially of trifluoroacetyl chloride (TFAC).

Aspect 14 is the method of any of Aspects 8-13, wherein the bottoms product includes sulfur dioxide ($SO_2$) in an amount of about 100 ppm or less.

Aspect 15 is the method of Aspect 7, further comprising the steps of: contacting a feed stream comprising a mixture of trifluoroacetyl chloride (TFAC) and sulfur dioxide ($SO_2$) with a solid adsorbent or a mixture of two or more solid adsorbents; and collecting a product stream consisting essentially of trifluoroacetyl chloride (TFAC).

Aspect 16 is the method of any of Aspects 10-15, wherein the solid adsorbent is chosen from the group consisting of molecular sieves, zeolite powder, silica gel, activated alumina, and activated carbon.

Aspect 17 is the method of any of Aspects 10-16, wherein the solid adsorbent is molecular sieves.

Aspect 18 is a method of separating trifluoroacetyl chloride (TFAC) and sulfur dioxide ($SO_2$) from a composition comprising trifluoroacetyl chloride (TFAC), sulfur dioxide ($SO_2$), and at least one impurity, comprising the steps of forming an azeotrope or azeotrope-like composition consisting essentially of effective amounts of trifluoroacetyl chloride (TFAC) and sulfur dioxide ($SO_2$) having a boiling point between about −30° C.±3° C. and about 90.0° C.±3° C. at a pressure of between about 5 psia±0.3 psia and about 450 psia±0.3 psia; and separating the azeotrope or azeotrope-like composition from the composition and the at least one impurity.

Aspect 19 is a method of synthesizing trifluoroacetyl iodide (TFAI) comprising: contacting a feed stream comprising trifluoroacetyl chloride (TFAC) with a feed stream comprising hydrogen iodide (HI) to provide a product stream comprising trifluoroacetyl iodide (TFAI).

Aspect 20 is the method of Aspect 19, wherein the molar ratio of trifluoroacetyl chloride (TFAC) to hydrogen iodide (HI) is 1:2 or less.

Aspect 21 is the method of either Aspect 19 or Aspect 20, further comprising removing sulfur dioxide ($SO_2$) from the product stream.

Aspect 22 is a composition comprising an azeotrope or azeotrope-like composition consisting essentially of effective amounts of trifluoroacetyl chloride (TFAC) and sulfur dioxide ($SO_2$).

Aspect 23 The composition of Aspect 22, wherein the azeotrope or azeotrope-like composition has a boiling point of about 10.0° C.±3° C. at a pressure of about 45 psia±0.3 psia.

Aspect 24 is a method of removing sulfur dioxide ($SO_2$) from trifluoroacetyl chloride (TFAC), the method comprising at least one of distillation, adsorption, or a combination thereof.

Aspect 25 is the method of any one of Aspect 24 or Aspects 8-21, further comprising the steps of: conveying a feed stream to a distillation column, the feed stream comprising trifluoroacetyl chloride (TFAC) and sulfur dioxide ($SO_2$); collecting the distillate from the distillation column, the distillate comprising trifluoroacetyl chloride and sulfur dioxide ($SO_2$); and collecting a bottoms product from the distillation column, the bottoms product consisting essentially of trifluoroacetyl chloride (TFAC).

Aspect 26 is the method of any one of Aspect 24, 25 or 8-21, further comprising the steps of: conveying a feed stream to a distillation column, the feed stream comprising trifluoroacetyl chloride (TFAC) and sulfur dioxide ($SO_2$); forming an azeotrope or azeotrope-like composition consisting essentially of effective amounts of trifluoroacetyl chloride (TFAC) and sulfur dioxide ($SO_2$); collecting the distillate from the distillation column, the distillate comprising the azeotrope or azeotrope-like composition; and collecting a bottoms product from the distillation column, the bottoms product consisting essentially of trifluoroacetyl chloride (TFAC).

Aspect 27 is the method of any one of Aspects 24-25 or 8-21, further comprising the steps of: conveying a feed stream to a distillation column, the feed stream comprising trifluoroacetyl chloride (TFAC), sulfur dioxide ($SO_2$); forming an azeotrope or azeotrope-like composition consisting essentially of effective amounts of trifluoroacetyl chloride (TFAC) and sulfur dioxide (SO$_2$); collecting the distillate from the distillation column, the distillate comprising the azeotrope or azeotrope-like composition; collecting a bottoms product from the distillation column; contacting the bottoms product from the distillation column with a solid adsorbent; and collecting a product stream consisting essentially of trifluoroacetyl chloride (TFAC).

Aspect 28 is the method of any one of Aspects 24-27 or 8-21, further comprising the steps of: conveying a feed stream to a distillation column, the feed stream comprising trifluoroacetyl chloride (TFAC), sulfur dioxide (SO$_2$); forming an azeotrope or azeotrope-like composition consisting essentially of effective amounts of trifluoroacetyl chloride (TFAC) and sulfur dioxide (SO$_2$); collecting a bottoms product from the distillation column; collecting the distillate from the column, the distillate comprising the azeotrope or azeotrope-like composition; contacting the distillate with a solid adsorbent; and collecting a product stream consisting essentially of trifluoroacetyl chloride (TFAC).

Aspect 29 is the method of any one of Aspects 24-28 or 8-21, further comprising the steps of: conveying a feed stream to a distillation column, the feed stream comprising trifluoroacetyl chloride (TFAC), sulfur dioxide (SO$_2$); forming an azeotrope or azeotrope-like composition consisting essentially of effective amounts of trifluoroacetyl chloride (TFAC) and sulfur dioxide (SO$_2$); collecting a bottoms product from the distillation column; contacting the bottoms product from the distillation column with a first solid adsorbent; collecting a product stream consisting essentially of trifluoroacetyl chloride (TFAC); collecting a distillate from the column, the distillate comprising the azeotrope or azeotrope-like composition; contacting the distillate from the distillation column with a second solid adsorbent; and collecting a product stream consisting essentially of trifluoroacetyl chloride (TFAC).

Aspect 30 is the method of any one of Aspects 24-29 or 8-21, further comprising the steps of: contacting a feed stream with a first solid adsorbent, the feed stream comprising trifluoroacetyl chloride (TFAC) and sulfur dioxide (SO$_2$); collecting a product stream comprising trifluoroacetyl chloride (TFAC) and sulfur dioxide (SO$_2$); conveying the product stream comprising trifluoroacetyl chloride (TFAC) and sulfur dioxide (SO$_2$) to a distillation column; forming an azeotrope or azeotrope-like composition consisting essentially of effective amounts of trifluoroacetyl chloride (TFAC) and sulfur dioxide (SO$_2$); collecting a bottoms product from the distillation column; contacting the bottoms product from the distillation column with a second solid adsorbent; collecting a product stream consisting essentially of trifluoroacetyl chloride (TFAC); collecting a distillate from the column, the distillate comprising the azeotrope or azeotrope-like composition; contacting the distillate from the distillation column with a third solid adsorbent; and collecting from the third solid adsorbent a product stream consisting essentially of trifluoroacetyl chloride (TFAC).

Aspect 31 is the method of any one of Aspects 24, 25, 27-30 or 8-21, wherein the bottoms product includes sulfur dioxide (SO$_2$) in an amount of about 100 ppm or less.

Aspect 32 is the method of any one of Aspects 24 or 8-21, further comprising the steps of: contacting a feed stream comprising a mixture of trifluoroacetyl chloride (TFAC) and sulfur dioxide (SO$_2$) with a solid adsorbent or a mixture of two or more solid adsorbents; and collecting a product stream consisting essentially of trifluoroacetyl chloride (TFAC).

Aspect 33 is the method of any one of Aspects 24, 32, or 8-21, the method of claim 11, wherein the solid adsorbent comprises one or more of molecular sieves, carbon molecular sieves, zeolite powder, silica gel, activated alumina, activated carbon, and combinations of the foregoing.

Aspect 34 is the method of Aspect 33, wherein the solid adsorbent is carbon molecular sieves.

Aspect 35 is a method of removing sulfur dioxide (SO$_2$) from a mixture comprising trifluoroacetyl iodide (TFAI), the method comprising at least one of distillation, adsorption, or a combination thereof.

Aspect 36 is the method of any one of Aspects 35 or 8-21, comprising: conveying a stream comprising trifluoroacetyl iodide (TFAI), hydrogen chloride (HCl), trifluoroacetyl chloride (TFAC), sulfur dioxide (SO$_2$), and hydrogen iodide (HI) to a first distillation column to provide a first overhead product and a first bottoms product; conveying the overhead product to a second distillation column to provide a second overhead product and a second bottoms product; and conveying the second bottoms product to an adsorption column to provide a product stream comprising trifluoroacetyl chloride (TFAC).

Aspect 37 is the method of any one of Aspect 35, 36, or 8-21, wherein the adsorption column comprises one or more of molecular sieves, carbon molecular sieves, zeolite powder, silica gel, activated alumina, activated carbon, and combinations of the foregoing.

Aspect 38 is the method of Aspect 37, wherein the adsorption column comprises carbon molecular sieves.

Aspect 39 is the method of any one of Aspects 24-38, wherein the stream comprising trifluoroacetyl iodide (TFAI), hydrogen chloride (HCl), trifluoroacetyl chloride (TFAC), sulfur dioxide (SO$_2$), and hydrogen iodide (HI) includes sulfur dioxide (SO$_2$) in an amount of 250 ppm or less. 1

Aspect 40 is the method of Aspect 39, comprising: conveying a stream comprising trifluoroacetyl iodide (TFAI), hydrogen chloride (HCl), hydrogen iodide (HI), trifluoroacetyl chloride (TFAC), and sulfur dioxide (SO$_2$ to a first distillation column to provide a first overhead product and a first bottoms product; conveying the first bottoms product to a second distillation column to provide a second overhead product and a second bottoms product; conveying the second bottoms product to a third distillation column to provide a third overhead product comprising trifluoroacetyl chloride (TFAC) and sulfur dioxide (SO$_2$) and a third bottoms product comprising trifluoroacetyl iodide (TFAI).

The invention claimed is:

1. A method for removing sulfur dioxide (SO$_2$) from trifluoroacetyl chloride (TFAC), comprising the steps of:
    conveying a feed stream to a distillation column, the feed stream comprising trifluoroacetyl chloride (TFAC) and sulfur dioxide (SO$_2$);
    forming an azeotrope or azeotrope-like composition consisting essentially of effective amounts of trifluoroacetyl chloride (TFAC) and sulfur dioxide (SO$_2$);
    collecting the distillate from the distillation column, the distillate comprising the azeotrope or azeotrope-like composition; and
    collecting a bottoms product from the distillation column, the bottoms product consisting essentially of trifluoroacetyl chloride (TFAC).

2. A method for removing sulfur dioxide (SO$_2$) from trifluoroacetyl chloride (TFAC), comprising the steps of:
    conveying a feed stream to a distillation column, the feed stream comprising trifluoroacetyl chloride (TFAC), and sulfur dioxide (SO$_2$);

forming an azeotrope or azeotrope-like composition consisting essentially of effective amounts of trifluoroacetyl chloride (TFAC) and sulfur dioxide ($SO_2$);

collecting the distillate from the distillation column, the distillate comprising the azeotrope or azeotrope-like composition;

collecting a bottoms product from the distillation column;

contacting the bottoms product from the distillation column with a solid adsorbent; and collecting a product stream consisting essentially of trifluoroacetyl chloride (TFAC).

3. The method of claim 1, further comprising the steps of:
contacting the distillate with a solid adsorbent; and
collecting a product stream consisting essentially of trifluoroacetyl chloride (TFAC).

4. The method of claim 1, further comprising the steps of:
contacting the bottoms product from the distillation column with a first solid adsorbent;
collecting a product stream consisting essentially of trifluoroacetyl chloride (TFAC);
contacting the distillate from the distillation column with a second solid adsorbent; and
collecting a product stream consisting essentially of trifluoroacetyl chloride (TFAC).

5. The method of claim 1, further comprising, prior to the conveying step, the steps of:
contacting a feed stream with a first solid adsorbent, the feed stream comprising trifluoroacetyl chloride (TFAC) and sulfur dioxide ($SO_2$); and
collecting a product stream comprising trifluoroacetyl chloride (TFAC) and sulfur dioxide ($SO_2$).

6. The method of claim 5, wherein the bottoms product includes sulfur dioxide ($SO_2$) in an amount of about 100 ppm or less.

7. The method of claim 1, wherein the azeotrope or azeotrope-like composition comprises from about 25 wt. % to about 99 wt. % of trifluoroacetyl chloride (TFAC) and from about 1 wt. % to about 75 wt. % of sulfur dioxide ($SO_2$).

8. The method of claim 1, wherein the bottoms product includes sulfur dioxide ($SO_2$) in an amount of about 100 ppm or less.

9. The method of claim 3, wherein the bottoms product includes sulfur dioxide ($SO_2$) in an amount of about 100 ppm or less.

10. The method of claim 4, wherein the bottoms product includes sulfur dioxide ($SO_2$) in an amount of about 100 ppm or less.

11. The method of claim 2, wherein the azeotrope or azeotrope-like composition comprises from about 25 wt. % to about 99 wt. % of trifluoroacetyl chloride (TFAC) and from about 1 wt. % to about 75 wt. % of sulfur dioxide ($SO_2$).

12. The method of claim 2, further comprising the steps of:
contacting the distillate with a solid adsorbent; and
collecting a product stream consisting essentially of trifluoroacetyl chloride (TFAC).

13. The method of claim 12, wherein the bottoms product includes sulfur dioxide ($SO_2$) in an amount of about 100 ppm or less.

14. The method of claim 2, further comprising the steps of:
contacting the bottoms product from the distillation column with a first solid adsorbent;
collecting a product stream consisting essentially of trifluoroacetyl chloride (TFAC);
contacting the distillate from the distillation column with a second solid adsorbent; and
collecting a product stream consisting essentially of trifluoroacetyl chloride (TFAC).

15. The method of claim 14, wherein the bottoms product includes sulfur dioxide ($SO_2$) in an amount of about 100 ppm or less.

16. The method of claim 2, further comprising, prior to the conveying step, the steps of:
contacting a feed stream with a first solid adsorbent, the feed stream comprising trifluoroacetyl chloride (TFAC) and sulfur dioxide ($SO_2$); and
collecting a product stream comprising trifluoroacetyl chloride (TFAC) and sulfur dioxide ($SO_2$).

17. The method of claim 16, wherein the bottoms product includes sulfur dioxide ($SO_2$) in an amount of about 100 ppm or less.

18. The method of claim 2, wherein the solid adsorbent comprises one or more of carbon molecular sieves, zeolite powder, silica gel, activated alumina, activated carbon, and combinations of the foregoing.

19. The method of claim 18, wherein the solid adsorbent comprises carbon molecular sieves.

20. The method of claim 3, wherein the solid adsorbent comprises carbon molecular sieves.

* * * * *